United States Patent
Arters et al.

(10) Patent No.: US 11,254,646 B2
(45) Date of Patent: Feb. 22, 2022

(54) ULTRA-LOW MOLECULAR WEIGHT IMIDE CONTAINING QUATERNARY AMMONIUM SALTS HAVING SHORT HYDROCARBON TAILS

(71) Applicant: The Lubrizol Corporation, Wickliffe, OH (US)

(72) Inventors: David C. Arters, Solon, OH (US); David J. Moreton, Milford (GB); James H. Bush, Mentor, OH (US); Paul R. Stevenson, Belper (GB); Paul E. Adams, Willoughby, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 562 days.

(21) Appl. No.: 15/780,785

(22) PCT Filed: Dec. 2, 2016

(86) PCT No.: PCT/US2016/064638
§ 371 (c)(1),
(2) Date: Jun. 1, 2018

(87) PCT Pub. No.: WO2017/096175
PCT Pub. Date: Jun. 8, 2017

(65) Prior Publication Data
US 2020/0361891 A1     Nov. 19, 2020

Related U.S. Application Data

(60) Provisional application No. 62/262,100, filed on Dec. 2, 2015.

(51) Int. Cl.
*C07D 307/60* (2006.01)
*C10L 1/188* (2006.01)
(Continued)

(52) U.S. Cl.
CPC ............ *C07D 307/60* (2013.01); *C10L 1/143* (2013.01); *C10L 1/1883* (2013.01); *C10L 1/221* (2013.01);
(Continued)

(58) Field of Classification Search
CPC ....... C07D 307/60; C10L 1/224; C10L 1/143; C10L 10/04; C10L 1/1883; C10L 1/221;
(Continued)

(56) References Cited

U.S. PATENT DOCUMENTS

| 5,254,138 A | 10/1993 | Kurek | |
|---|---|---|---|
| 2008/0202561 A1* | 8/2008 | DuMont | C10L 1/023 134/20 |

(Continued)

FOREIGN PATENT DOCUMENTS

| WO | 02/102942 A1 | 12/2002 |
|---|---|---|
| WO | 2014/195464 A1 | 12/2014 |
| WO | 2015/183908 A1 | 12/2015 |

*Primary Examiner* — Ellen M McAvoy
*Assistant Examiner* — Chantel L Graham
(74) *Attorney, Agent, or Firm* — Iken S. Sans; Teresan W. Gilbert

(57) ABSTRACT

The present technology is related to imide containing quaternary ammonium salts having a hydrocarbyl substituent of number average molecular weight less 300, and additive packages having such quaternary ammonium salts and improved stability.

19 Claims, 4 Drawing Sheets

(51) Int. Cl.
  *C10L 1/224* (2006.01)
  *C10L 1/22* (2006.01)
  *C10L 1/14* (2006.01)
  *C10M 133/16* (2006.01)
  *C10L 10/04* (2006.01)

(52) U.S. Cl.
  CPC ............... *C10L 1/224* (2013.01); *C10L 10/04* (2013.01); *C10M 133/16* (2013.01); *C10L 2200/0423* (2013.01); *C10L 2200/0446* (2013.01); *C10L 2230/14* (2013.01)

(58) Field of Classification Search
  CPC ......... C10L 2200/0423; C10L 2230/14; C10L 2200/0446; C10M 133/16
  See application file for complete search history.

(56) References Cited

U.S. PATENT DOCUMENTS

| | | | |
|---|---|---|---|
| 2012/0010112 A1* | 1/2012 | Grabarse | C10L 1/22 508/291 |
| 2015/0024984 A1 | 1/2015 | Loper | |
| 2015/0232775 A1 | 8/2015 | Harle et al. | |
| 2015/0252278 A1 | 9/2015 | Bush et al. | |
| 2017/0096610 A1* | 4/2017 | Bush | C10L 1/232 |

\* cited by examiner

ULTRA-LOW MOLECULAR WEIGHT IMIDE CONTAINING QUATERNARY AMMONIUM SALTS HAVING SHORT HYDROCARBON TAILS

CROSS REFERENCE TO RELATED APPLICATION

This application claims priority from PCT Application Serial No. PCT/US2016/064638 filed on Dec. 2, 2016, which claims the benefit of U.S. Provisional Application No. 62/262,100 filed on Dec. 2, 2015, both of which are incorporated in their entirety by reference herein.

FIELD OF THE INVENTION

The present technology is related to imide containing quaternary ammonium salts having a hydrocarbyl substituent of number average molecular weight of less than 300, and the use of such quaternary ammonium salts to improve additive package stability. The technology further relates to the use of the quaternary ammonium salts in fuel and lubricant compositions and methods fueling or lubricating an internal combustion engine.

BACKGROUND OF THE INVENTION

Deposit formation in diesel fuel injector nozzles is highly problematic, resulting in incomplete diesel combustion, and therefore power loss and misfiring. Traditionally, polyisobutylene succinimide detergents have been used to inhibit injector fouling, but these materials have shown poor efficacy in modern engines. A new class of detergents based on quaternized polyisobutylene succinimides has been shown to provide improved detergency performance in both the traditional and modern diesel engines.

Detergents are frequently added to bulk fuel in the form of concentrated additive packages. In addition to detergents, the additive packages may contain one or more additional additives, including, but not limited to, demulsifiers and foam inhibitors. Detergents are known to have compatibility issues with some types of demulsifiers and foam inhibitors that result in stability problems causing separation of additive package components, or "liquid drop out". Additive package instability or liquid drop out can increase when the additive package is exposed to temperatures below room temperature. To increase the stability of additive packages, stabilizing solvents such as 2-ethylhexanol or heavy aromatic naphtha are added. Depending on the amount of demulsifier or foam inhibitor present, the solvent content can be quite high thereby increasing costs.

Thus, there is a need for concentrated additive packages that remain stable when the amount of solvent is decreased.

SUMMARY OF THE INVENTION

It was surprisingly found that ultra-low molecular weight quaternized additives having short hydrocarbon tails that, when used in additive packages, increase the stability of the additive package as compared to quaternized additives having longer hydrocarbon tails. Thus, the amount of solvent required can be reduced thereby resulting in concentrated additive packages that perform more efficiently. It has been found that quaternary ammoniums salts prepared from hydrocarbyl substituted acylating agents, such as, for example, dodecenyl succinic acids or anhydrides, having a hydrocarbyl substituent with a number average molecular weight ($M_n$) of less than 300, result in quaternary ammonium salts that provide improved stability performance compared to quaternary ammonium salts prepared from hydrocarbyl substituted acylating agents having a hydrocarbyl substituent with a number average molecular weight of greater than 1000 $M_n$. The number average molecular weight ($M_n$) may be measured using gel permeation chromatography (GPC) based on polystyrene standards.

Thus, in one aspect the present technology provides a composition including an imide containing quaternary ammonium salt with a $M_n$ less than 300 ("imide quat"). The imide quat itself can be the reaction product of (a) a quaternizable compound and (b) a quaternizing agent suitable for converting a quaternizable amino group of the nitrogen containing compound to a quaternary nitrogen. The quaternizable compound can be the reaction product of (i) a hydrocarbyl-substituted acylating agent, and (ii) a nitrogen containing compound having a nitrogen atom capable of reacting with the hydrocarbyl-substituted acylating agent to form an imide, and further having at least one quaternizable amino group. The hydrocarbyl-substituent of the hydrocarbyl-substituted acylating agent can have a number average molecular weight less than 300.

In an embodiment, the quaternizable amino group can be a primary, secondary or tertiary amino group. In a further embodiment, the hydrocarbyl-substituted acylating agent may be at least one of dodecenyl succinic anhydride, dodecenyl succinic acid, hexadecenyl succinic anhydride, hexadecenyl succinic acid, octadecenyl succinic anhydride, octadecenyl succinic acid, or mixtures thereof.

In some embodiments, the reaction to prepare the quaternizable compound of (a) can be carried out at a temperature of greater than 80 or 90 or 100° C. In some embodiments, the water of reaction, or water produced during the condensation reaction can be removed.

In other embodiments, the quaternizing agents can exclude methyl salicylate. In the same or different embodiments, the nitrogen containing compound can exclude dimethylaminopropylamine.

In still further embodiments, the quaternizing agent can be a dialkyl sulfate, an alkyl halide, a hydrocarbyl substituted carbonate, a hydrocarbyl epoxide, a carboxylate, alkyl esters, or mixtures thereof. In some cases the quaternizing agent can be a hydrocarbyl epoxide. In some cases the quaternizing agent can be a hydrocarbyl epoxide in combination with an acid. In some cases the quaternizing agent can be an oxalate or terephthalate. In one embodiment, the oxalate is dimethyl oxalate.

In some embodiments, the imide quats described above can further include at least one other additive. In some instances, the at least one other additive can be a foam inhibitor, a detergent, a demulsifier, a lubricating agent, a cold flow improver, an antioxidant, or a mixture thereof. In some instances the at least one other additive can be at least one non-quaternized hydrocarbyl-substituted succinic acid. In some instances, the at least one other additive can be at least one hydrocarbyl-substituted quaternary ammonium salt. In some instances where the at least one other additive is a non-quaternized or quaternized hydrocarbyl-substituted succinic acid, the hydrocarbyl-substituent can be a polyisobutylene having a number average molecular weight of 100 to 5000. In an embodiment, the at least one other additive can be at least one Mannich compound.

In another embodiment, the composition may further comprise a hydrolized alkenyl succinic acid or anhydride. In another embodiment, the hydrolized alkenyl succinic acid or anhydride may have a $M_n$ ranging from 225 to 1000. In yet another embodiment, the hydrolized alkenyl succinic acid or anhydride may have a $M_n$ of 550.

In another embodiment, a composition is disclosed comprising an imide salt and a hydrolized alkenyl succinic acid or anhydride with a molecular weight $M_n$ ranging from 225 to 1000. The imide quat may comprise the reaction product of (a) a quaternizable compound and (b) a quaternizing agent suitable for converting a quaternizable amino group of the nitrogen containing compound to a quaternary nitrogen. The quaternizable compound can be the reaction product of (i) a hydrocarbyl-substituted acylating agent, and (ii) a nitrogen containing compound having a nitrogen atom capable of reacting with the hydrocarbyl-substituted acylating agent to form an imide, and further having at least one quaternizable amino group. The hydrocarbyl-substituent of the hydrocarbyl-substituted acylating agent can have a number average molecular weight of less than 300.

A further aspect of the present technology includes a composition having an imide quat as described herein, and further having a fuel that is liquid at room temperature. In some embodiments the fuel can be a diesel fuel.

A further aspect of the present technology includes a composition having an imide quat as described herein, and further having an oil of lubricating viscosity.

A still further aspect of the present technology provides a method of operating an internal combustion engine. In one embodiment, the method can include the steps of (a) supplying to the engine a fuel composition and (b) operating said engine. The fuel composition employed in the foregoing method can include (i) a fuel which is liquid at room temperature, and (ii) a composition comprising an imide quat as described herein. In another embodiment, the method of operating an internal combustion engine can include the steps of (a) supplying a lubricating oil composition to the crankcase of the engine and (b) operating said engine. The lubricating oil composition can include (i) oil of lubricating viscosity, and (ii) a composition comprising an imide quat as described herein.

In another embodiment, additives packages having improved stability comprising an imide quat are disclosed. The imide quat may comprise the reaction product of (a) a quaternizable compound and (b) a quaternizing agent suitable for converting a quaternizable amino group of the nitrogen containing compound to a quaternary nitrogen. The quaternizable compound can be the reaction product of (i) a hydrocarbyl-substituted acylating agent, and (ii) a nitrogen containing compound having a nitrogen atom capable of reacting with the hydrocarbyl-substituted acylating agent to form an imide, and further having at least one quaternizable amino group. The hydrocarbyl-substituent of the hydrocarbyl-substituted acylating agent can have a number average molecular weight less than 300. These additive packages require less stabilizing solvent than additive packages comprising imide quats made with hydrocarbyl-substituted acylating agents having higher number average molecular weights (M), such as greater than 300, or 550 or 1000.

Embodiments of the present technology may provide the use of an imide quat for at least one of antiwear performance, friction modification (particularly for enhancing fuel economy), detergent performance (particularly deposit control or varnish control), dispersancy (particularly soot control, sludge control, or corrosion control).

In one embodiment, a composition comprising an imide containing quaternary ammonium salt with a number average molecular weight of less than 300 ("imide quat") is disclosed. The imide quat may comprise the reaction product of a quaternizable compound and a quaternizing agent suitable for converting the quaternizable amino group of the nitrogen containing compound to a quaternary nitrogen. The quaternizable compound may be the reaction product of a hydrocarbyl-substituted acylating agent, wherein the hydrocarbyl-substituent has a number average molecular weight of less than 300, and a nitrogen containing compound having a nitrogen atom capable of reacting with the hydrocarbyl-substituted acylating agent to form an imide, and further having at least one quaternizable amino group. The quaternizable amino group may be a primary, secondary or tertiary amino group.

In one embodiment, the hydrocarbyl-substituted acylating agent may be polyisobutenyl succinic anhydride or polyisobutenyl succinic acid. In yet another embodiment, the reaction of the hydrocarbyl-substituted acylating agent and the nitrogen containing compound may be carried out at a temperature of greater than 80° C.

In one embodiment, the nitrogen containing compound excludes compounds comprising dimethylaminopropylamine.

In another embodiment, the quaternizing agent comprises at least one dialkyl sulfate, alkyl halide, hydrocarbyl substituted carbonate, hydrocarbyl epoxide, carboxylate, alkyl ester or mixtures thereof. In one embodiment, the quaternizing agent may be a hydrocarbyl epoxide. Alternatively, the quaternizing agent may be a hydrocarbyl epoxide in combination with an acid. In another embodiment, the quaternizing agent may be an oxalate or terephthalate. In yet another embodiment, the quaternizing agent excludes methyl salicylate.

The disclosed compositions comprising an imide containing quaternary ammonium salt with a number average molecular weight of less than 300 ("imide quat") may further comprise at least one other additive. Suitable additives include, but are not limited to, foam inhibitors, detergents, dispersants, demulsifiers, lubricity agents, cold flow improvers, antioxidants, or mixtures thereof.

In one embodiment, the at least one other additive comprises at least one hydrocarbyl-substituted succinic acid or at least one hydrocarbyl-substituted quaternary ammonium salt. The hydrocarbyl-substituent may be a polyisobutylene having a number average molecular weight ranging from 100 to 5000.

In another embodiment, the at least one other additive comprises at least one detergent/dispersant that is an amphiphilic substance which possess at least one hydrophobic hydrocarbon radical with a number average molecular weight of 100 to 10000 and at least one polar moiety selected from (i) Mono- or polyamino groups having up to 6 nitrogen atoms, at least one nitrogen atom having basic properties; (ii) Hydroxyl groups in combination with mono or polyamino groups, at least one nitrogen atoms having basic properties; (v) Polyoxy-$C_2$ to $C_4$ alkylene moieties terminated by hydroxyl groups, mono- or polyamino groups, at least one nitrogen atom having basic properties, or by carbamate groups; (vii) Moieties derived from succinic anhydride and having hydroxyl and/or amino and/or amido and/or imido groups; and/or (viii) Moieties obtained by Mannich reaction of substituted phenols with aldehydes and mono- or polyamines. In yet another embodiment, the at least one other additive may comprise at least one Mannich compound.

In another embodiment, the disclosed compositions may further comprise a fuel that is liquid at room temperature. The fuel may be gasoline or diesel. The fuel composition may comprise at least one of a low number average molecular weight soap, a low number average molecular weight polyisobutylene succinimide (PIBSI), or a mixture thereof. The low molecular weight soap may have a number average molecular weight ($M_n$) of less than 340.

In yet another embodiment, the fuel composition may comprise 0.01 to 25 ppm of a metal and 1 to 12 ppm of a corrosion inhibitor. The corrosion inhibitor may be an alkenyl succinic acid comprising at least one of dodecenyl succinic acid (DDSA), hexadecenyl succinic acid (HDSA), or mixtures thereof.

In yet another embodiment, the fuel composition comprises PIBSI with a low number average molecular weight $M_n$ of less than 400.

In yet another method, the composition comprising an imide quat may further comprise an oil of lubricating viscosity.

A method of operating an internal combustion engine is also disclosed. The method may comprise supplying a fuel which is liquid at room temperature having a composition comprising an imide quat therein to the engine and operating the engine. The imide quat may be added to the fuel in an amount ranging from 5 to 1000 ppm by weight based on a total weight of the fuel composition.

In yet another embodiment, the method of operating an internal combustion engine may comprise supplying an oil of lubricating viscosity having a composition comprising an imide quat therein to the engine crankcase and operating the engine. The imide quat may be added to the oil on an active basis 1-5 wt %. The oil of lubricating viscosity may have a total sulfated ash of less than 1 wt % and/or a phosphorus content of less than 0.11 wt %.

A method of reducing and/or preventing injector deposits is also disclosed. The method may comprise supplying a fuel composition having a composition comprising an imide quat therein to a fuel injector of the engine and operating the engine. The deposits may be internal diesel injector deposits (IDID). In yet another embodiment, the deposits may comprise a low number average molecular weight soap, a low number average molecular weight polyisobutylene succinimide (PIBSI), or mixtures thereof.

In another embodiment, the fuel may comprise a molecular weight soap with a number average molecular weight ($M_n$) of less than 340.

In another embodiment, the fuel may comprise 0.01 to 25 ppm of a metal and 1 to 12 ppm of a corrosion inhibitor. In yet another embodiment, the corrosion inhibitor may be an alkenyl succinic acid comprising at least one of dodecenyl succinic acid (DDSA), hexadecenyl succinic acid (HDSA), or mixtures thereof.

In another embodiment, the fuel comprises a PIBSI with a low number average molecular weight $M_n$ of less than 400. The fuel may be gasoline or diesel. In yet another embodiment, the engine may comprise a high pressure common rail injector system.

The use of a composition comprising an imide quat to reduce and/or prevent internal deposits in an engine operated with a gasoline or diesel fuel is also disclosed. In one embodiment, the engine may comprise a high pressure common rail injector system. In yet another embodiment, the imide quat may be used to reduce and/or prevent internal diesel injector deposits (IDID).

In another embodiment, an additive package having improved stability is disclosed. The additive package may comprise a composition including an imide quat as described above. In another embodiment, a method of improving additive package stability by adding an imide quat as described above to the additive package. In yet another embodiment, the use of an imide quat as described above to improve additive package stability is disclosed.

DETAILED DESCRIPTION OF THE INVENTION

Figure 1:
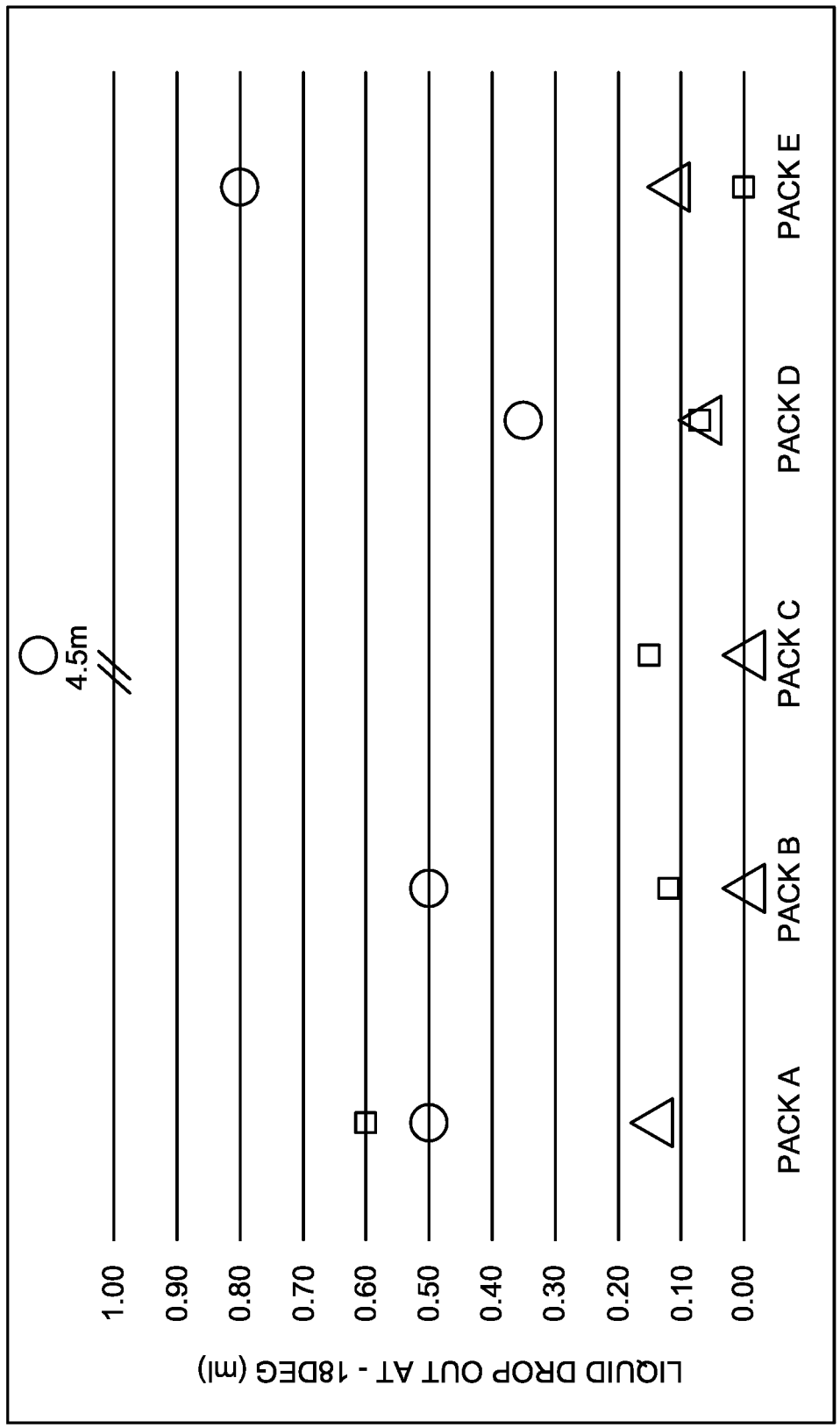
FIG. 1 shows the additive package stability test results of an embodiment of the disclosed technology.

Various features and embodiments will be described below by way of non-limiting illustration.

One aspect of the current technology relates to a composition comprising an imide containing quaternary ammonium salt with a number average molecular weight ("$M_n$") less than 300 ("imide quat"). These imide quats have short hydrocarbon tails that, when used in additive packages, increase the stability of the additive package as compared to imide quats having longer hydrocarbon tails. Without limiting the disclosed technology to one theory of operation, it is believed that the shorter tails make the quats more protic and less hydrophobic thereby making them more compatible with other additives present in the additive package and increasing the additive package stability. As such, less stabilizing solvents are required and the additive packages are more concentrated.

The number average molecular weight of the materials described herein is measured using gas permeation chromatography (GPC) using a Waters GPC 2000 equipped with a refractive index detector and Waters Empower™ data acquisition and analysis software. The columns are polystyrene (PLgel, 5 micron, available from Agilent/Polymer Laboratories, Inc.). For the mobile phase, individual samples are dissolved in tetrahydrofuran and filtered with PTFE filters before they are injected into the GPC port.

Waters GPC 2000 Operating Conditions:
Injector, Column, and Pump/Solvent compartment temperatures: 40° C.
Autosampler Control: Run time: 40 minutes
Injection volume: 300 microliter
Pump: System pressure: ~90 bars (Max. pressure limit: 270 bars, Min. pressure limit: 0 psi)
Flow rate: 1.0 ml/minute
Differential Refractometer (RI): Sensitivity: −16; Scale factor: 6

Imide Containing Quaternary Ammonium Salt ("Imide Quat")

The production of a quaternary ammonium salt generally results in a mixture of compounds including a quaternary ammonium salt or salts, and this mixture may be difficult to define apart from the process steps employed to produce the quaternary ammonium salt. Further, the process by which a quaternary ammonium salt is produced can be influential in imparting distinctive structural characteristics to the final quaternary ammonium salt product that can affect the properties of the quaternary ammonium salt product. Thus, in one embodiment, the imide quat of the present technology may be described as a reaction product of (a) a quaternizable compound, and (b) a quaternizing agent. As used herein, reference to imide quat(s) includes reference to the mixture compounds having a number average molecular weight of less than 300, including a quaternary ammonium salt or salts as described herein, as well as referring to the quaternary ammonium salt itself.

The quaternizable compound of (a) employed to prepare the imide quat itself may be the reaction product of (i) a hydrocarbyl-substituted acylating agent, and (ii) a nitrogen containing compound. More particularly, the hydrocarbyl-substituted acylating agent of (a)(i) can consist of an acylating agent functionalized with a hydrocarbyl-substituent having a number average molecular weight of less than 300.

Examples of quaternary ammonium salts and methods for preparing the same are described in the following patents, which are hereby incorporated by reference, U.S. Pat. Nos. 4,253,980, 3,778,371, 4,171,959, 4,326,973, 4,338,206, 5,254,138, and 7,951,211.

Details regarding the quaternizable compound, and specifically, the hydrocarbyl-substituted acylating agent and the nitrogen containing compound, as well as the quaternizing agent, are provided below.

The Hydrocarbyl Substituted Acylating Agent

The hydrocarbyl substituted acylating agent employed to prepare the quaternizable compound can be the reaction product of the precursor to the hydrocarbyl-substituent, which is a long chain hydrocarbon, generally a polyolefin, with a monounsaturated carboxylic acid reactant such as (i) α,β-monounsaturated $C_4$ to $C_{10}$ dicarboxylic acid such as fumaric acid, itaconic acid, maleic acid; (ii) derivatives of (i) such as anhydrides or $C_1$ to $C_5$ alcohol derived mono- or di-esters of (i).

The hydrocarbyl-substituent is a hydrocarbyl group with a chain of less than 20 carbon atoms. In one embodiment, the hydrocarbyl group can have a number average molecular weight ($M_n$) of less than 300. The $M_n$ of the hydrocarbyl-substituent can also be equal to or less than 250, or 200, or 150, or even less than 100. In an embodiment, the hydrocarbyl-substituent can be any compound containing an olefinic bond represented by the general formula:

$$(R^1)(R^2)C=C(R^6)(CH(R^7)(R^8)) \quad (I)$$

wherein each of $R^1$ and $R^2$ is, independently, hydrogen or a hydrocarbon based group. Each of $R^6$, $R^7$ and $R^8$ is, independently, hydrogen or a hydrocarbon based group; preferably at least one is a hydrocarbon based group containing less than 20 carbon atoms. In yet other embodiments, the hydrocarbon based group may be a $C_8$ to $C_{18}$ or a $C_{12}$ to $C_{18}$ hydrocarbon based group.

Olefin polymers for reaction with the monounsaturated carboxylic acids can include polymers comprising a major molar amount of $C_2$ to $C_{20}$, e.g. $C_2$ to $C_5$ monoolefin. Such olefins include ethylene, propylene, butylene, isobutylene, pentene, octene-1, or styrene. The polymers can be homopolymers such as polyisobutylene, as well as copolymers of two or more of such olefins such as copolymers of, ethylene and propylene; butylene and isobutylene; propylene and isobutylene. Other copolymers include those in which a minor molar amount of the copolymer monomers e.g., 1 to 10 mole % is a $C_4$ to $C_{18}$ diolefin, e.g., a copolymer of isobutylene and butadiene; or a copolymer of ethylene, propylene and 1,4-hexadiene.

In other embodiments, at least one R of formula (I) may be dodecene, hexadecene, octadecene, or mixtures thereof. In one embodiment, at least one R of formula (I) is derived from polybutene, that is, polymers of C4 olefins, including 1-butene, 2-butene and isobutylene. C4 polymers can include polyisobutylene. In another embodiment, at least one R of formula (I) is derived from ethylene-alpha olefin polymers, including ethylene-propylene-diene polymers. Ethylene-alpha olefin copolymers and ethylene-lower olefin-diene terpolymers are described in numerous patent documents, including European patent publication EP 0 279 863 and the following U.S. Pat. Nos. 3,598,738; 4,026,809; 4,032,700; 4,137,185; 4,156,061; 4,320,019; 4,357,250; 4,658,078; 4,668,834; 4,937,299; 5,324,800 each of which are incorporated herein by reference for relevant disclosures of these ethylene based polymers.

In another embodiment, the olefinic bonds of formula (I) are predominantly vinylidene groups, represented by the following formulas:

wherein R is a hydrocarbyl group

wherein R is a hydrocarbyl group.

In one embodiment, the vinylidene content of formula (I) can comprise at least 30 mole % vinylidene groups, at least 50 mole % vinylidene groups, or at least 70 mole % vinylidene groups. Such material and methods for preparing them are described in U.S. Pat. Nos. 5,071,919; 5,137,978; 5,137,980; 5,286,823, 5,408,018, 6,562,913, 6,683,138, 7,037,999 and U.S. Publication Nos. 20040176552A1, 20050137363 and 20060079652A1, which are expressly incorporated herein by reference, such products are commercially available by BASF, under the trade name GLISSOPAL® and by Texas PetroChemical LP, under the trade name TPC 1105™ and TPC 595™.

In other embodiments, the hydrocarbyl-substituted acylating agent may be a "conventional" vinylidene polyisobutylene (PIB) wherein less than 20% of the head groups are vinylidene head groups as measured by nuclear magnetic resonance (NMR). Alternatively, the hydrocarbyl-substituted acylating agent may be a mid-vinylidene PIB or a high-vinylidene PIB. In mid-vinylidene PIBs, the percentage of head groups that are vinylidene groups can range from greater than 20% to 70%. In high-vinylidene PIBs, the percentage of head groups that are vinylidene head groups is greater than 70%.

Methods of making hydrocarbyl substituted acylating agents from the reaction of the monounsaturated carboxylic acid reactant and the compound of formula (I) are well known in the art and disclosed in the following patents: U.S. Pat. Nos. 3,361,673 and 3,401,118 to cause a thermal "ene" reaction to take place; U.S. Pat. Nos. 3,087,436; 3,172,892; 3,272,746, 3,215,707; 3,231,587; 3,912,764; 4,110,349; 4,234,435; 6,077,909; 6,165,235 and are hereby incorporated by reference.

Nitrogen Containing Compound

The composition of the present invention contains a nitrogen containing compound having a nitrogen atom capable of reacting with the acylating agent and further having a quaternizable amino group. A quaternizable amino group is any primary, secondary or tertiary amino group on the nitrogen containing compound that is available to react with a quaternizing agent to become a quaternary amino group.

In one embodiment, the nitrogen containing compound can be represented by the following formulas:

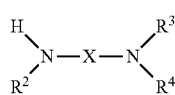

(VII)

wherein X is an alkylene group containing 1 to 4 carbon atoms; $R^2$ is hydrogen or a hydrocarbyl group; and $R^3$ and $R^4$ are hydrocarbyl groups.

Examples of the nitrogen containing compound capable of reacting with the acylating agent can include but is not limited to: dimethylaminopropylamine, N,N-dimethyl-aminopropylamine, N,N-diethyl-aminopropylamine, N,N-dimethyl-aminoethylamine ethylenediamine, 1,2-propylenediamine, 1,3-propylene diamine, isomeric amines, including butylenediamines, pentanediamines, hexanediamines, and heptanediamines, diethylenetriamine, dipropylenetriamine, dibutylenetriamine, triethylenetetramine, tetraethylenepentamine, pentaethylenehexamine, hexamethylenetetramine, and bis(hexamethylene) triamine, the diaminobenzenes, the diaminopyridines, N-methyl-3-amino-1-propylamine, or mixtures thereof. The nitrogen containing compounds capable of reacting with the acylating agent and further having a quaternizable amino group can further include aminoalkyl substituted heterocyclic compounds such as 1-(3-aminopropyl)imidazole and 4-(3-aminopropyl)morpholine, 1-(2-aminoethyl)piperidine, 3,3-diamino-N-methyldipropylamine. In some embodiments, the nitrogen containing compound excludes dimethylaminopropylamine.

In one embodiment, the nitrogen containing compound can be an imidazole, for example, as represented by the following formula:

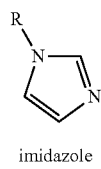

(IX)

imidazole wherein R is an amine capable of condensing with said hydrocarbyl-substituted acylating agent and having from 3 to 8 carbon atoms.

In one embodiment, the nitrogen containing compound can be represented by formula X:

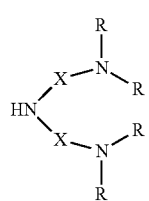

(X)

wherein each X can be, individually, a $C_1$ to $C_6$ hydrocarbylene group, and each R can be, individually, a hydrogen or a $C_1$ to $C_6$ hydrocarbyl group. In one embodiment, X can be, for example, a $C_1$, $C_2$ or $C_3$ alkylene group. In the same or different embodiments, each R can be, for example, H or a $C_1$, $C_2$ or $C_3$ alkyl group.

Quaternizable Compound

The hydrocarbyl substituted acylating agents and nitrogen containing compounds described above are reacted together to form a quaternizable compound. Methods and process for reacting the hydrocarbyl substituted acylating agents and nitrogen containing compounds are well known in the art.

In embodiments, the reaction between the hydrocarbyl substituted acylating agents and nitrogen containing compounds can be carried out at temperatures of greater than 80° C., or 90° C., or in some cases 100° C., such as between 100 and 150 or 200° C., or 125 and 175° C. At the foregoing temperatures water may be produced during the condensation, which is referred to herein as the water of reaction. In some embodiments, the water of reaction can be removed during the reaction, such that the water of reaction does not return to the reaction and further react.

The hydrocarbyl substituted acylating agents and nitrogen containing compounds may be reacted at a ratio of 1:1, but the reaction may also containing the respective reactants (i.e., hydrocarbyl substituted acylating agent:nitrogen containing compound) from 3:1 to 1:1.2, or from 2.5:1 to 1:1.1, and in some embodiments from 2:1 to 1:1.05.

Quaternizing Agent

The quaternary ammonium salt can be formed when the quaternizable compound, that is, the reaction products of the hydrocarbyl substituted acylating agent and nitrogen containing compounds described above, are reacted with a quaternizing agent. Suitable quaternizing agents can include, for example, dialkyl sulfates, alkyl halides, hydrocarbyl substituted carbonates; hydrocarbyl epoxides, carboxylates, alkyl esters, and mixtures thereof.

In one embodiment, the quaternizing agent can include alkyl halides, such as chlorides, iodides or bromides; alkyl sulfonates; dialkyl sulfates, such as, dimethyl sulfate and diethyl sulfate; sultones; alkyl phosphates; such as, C1-12 trialkylphosphates; di C1-12 alkylphosphates; borates; C1-12 alkyl borates; alkyl nitrites; alkyl nitrates; dialkyl carbonates, such as dimethyl oxalate; alkyl alkanoates, such as methylsalicylate; O,O-di-C1-12 alkyldithiophosphates; or mixtures thereof.

In one embodiment, the quaternizing agent may be derived from dialkyl sulfates such as dimethyl sulfate or diethyl sulfate, N-oxides, sultones such as propane and butane sultone; alkyl, acyl or aryl halides such as methyl and ethyl chloride, bromide or iodide or benzyl chloride, and a hydrocarbyl (or alkyl) substituted carbonates. If the alkyl halide is benzyl chloride, the aromatic ring is optionally further substituted with alkyl or alkenyl groups.

The hydrocarbyl (or alkyl) groups of the hydrocarbyl substituted carbonates may contain 1 to 50, 1 to 20, 1 to 10 or 1 to 5 carbon atoms per group. In one embodiment, the hydrocarbyl substituted carbonates contain two hydrocarbyl groups that may be the same or different. Examples of suitable hydrocarbyl substituted carbonates include dimethyl or diethyl carbonate.

In another embodiment, the quaternizing agent can be a hydrocarbyl epoxide, for example, as represented by the following formula:

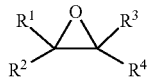

(XII)

wherein $R^1$, $R^2$, $R^3$ and $R^4$ can be independently H or a hydrocarbyl group contain from 1 to 50 carbon atoms. Examples of hydrocarbyl epoxides include: ethylene oxide, propylene oxide, butylene oxide, styrene oxide and combinations thereof. In one embodiment the quaternizing agent does not contain any styrene oxide.

In some embodiments, the hydrocarbyl epoxide can be an alcohol functionalized epoxide, C4 to C14 epoxides, and mixtures thereof. Exemplary C4 to C14 epoxides are those of formula XII where $R^1$, $R^2$, $R^3$ and $R^4$ can be independently H or a C2 to C12 hydrocarbyl group. In an embodiment, the epoxides can be C4 to C14 epoxides. Epoxides suitable as quaternizing agents in the present technology can include, for example, C4 to C14 epoxides having linear hydrocarbyl substituents, such as, for example, 2-ethyloxirane, 2-propyloxirane, and the like, and C4 to C14 epoxides having branched and cyclic or aromatic substituents, such as, for example, styrene oxide. C4 to C14 epoxides can also include epoxidized tri-glycerides, fats or oils; epoxidized alkyl esters of fatty acids; and mixtures thereof. In yet another embodiment, the hydrocarbyl epoxide may be a C4-C20 epoxide.

Exemplary alcohol functionalized epoxides can include those of formula XII where $R^1$, $R^2$, $R^3$ and $R^4$ can be independently H or a hydroxyl containing hydrocarbyl group. In an embodiment, hydroxyl containing hydrocarbyl group can contain from 2 to 32, or from 3 to 28, or even from 3 to 24 carbon atoms. Exemplary alcohol functionalized epoxide derivatives can include for example, glycidol and the like.

In some embodiments the hydrocarbyl epoxide can be employed in combination with an acid. The acid used with the hydrocarbyl epoxide may be a separate component, such as acetic acid. In other embodiments, a small amount of an acid component may be present, but at <0.2 or even <0.1 moles of acid per mole of hydrocarbyl acylating agent. These acids may also be used with the other quaternizing agents described above, including the hydrocarbyl substituted carbonates and related materials described below.

In some embodiments the quaternizing agent does not contain any substituent group that contains more than 20 carbon atoms.

In another embodiment the quaternizing agent can be an ester of a carboxylic acid capable of reacting with a tertiary amine to form a quaternary ammonium salt, or an ester of a polycarboxylic acid. In a general sense such materials may be described as compounds having the structure:

(XIII)

where $R^{19}$ is an optionally substituted alkyl, alkenyl, aryl or alkylaryl group and $R^{20}$ is a hydrocarbyl group containing from 1 to 22 carbon atoms.

Suitable compounds include esters of carboxylic acids having a pKa of 3.5 or less. In some embodiments the compound is an ester of a carboxylic acid selected from a substituted aromatic carboxylic acid, an α-hydroxycarboxylic acid and a polycarboxylic acid. In some embodiments the compound is an ester of a substituted aromatic carboxylic acid and thus $R^{19}$ is a substituted aryl group. $R^{19}$ may be a substituted aryl group having 6 to 10 carbon atoms, a phenyl group, or a naphthyl group. $R^{19}$ may be suitably substituted with one or more groups selected from carboalkoxy, nitro, cyano, hydroxy, SR' or NR'R" where each of R' and R" may independently be hydrogen, or an optionally substituted alkyl, alkenyl, aryl or carboalkoxy groups. In some embodiments R' and R" are each independently hydrogen or an optionally substituted alkyl group containing from 1 to 22, 1 to 16, 1 to 10, or even 1 to 4 carbon atoms.

In some embodiments $R^{19}$ in the formula above is an aryl group substituted with one or more groups selected from hydroxyl, carboalkoxy, nitro, cyano and $NH^2$. $R^{19}$ may be a poly-substituted aryl group, for example trihydroxyphenyl, but may also be a mono-substituted aryl group, for example an ortho substituted aryl group. $R^{19}$ may be substituted with a group selected from OH, $NH_2$, $NO_2$, or COOMe. Suitably $R^{19}$ is a hydroxy substituted aryl group. In some embodiments $R^{19}$ is a 2-hydroxyphenyl group. $R^{21}$ may be an alkyl or alkylaryl group, for example an alkyl or alkylaryl group containing from 1 to 16 carbon atoms, or from 1 to 10, or 1 to 8 carbon atoms. $R^2$ may be methyl, ethyl, propyl, butyl, pentyl, benzyl or an isomer thereof. In some embodiments $R^{20}$ is benzyl or methyl. In some embodiments the quaternizing agent is methyl salicylate. In some embodiments the quaternizing agent excludes methyl salicylate.

In some embodiments the quaternizing agent is an ester of an alpha-hydroxycarboxylic acid. Compounds of this type suitable for use herein are described in EP 1254889. Examples of suitable compounds which contain the residue of an alpha-hydroxycarboxylic acid include (i) methyl-, ethyl-, propyl-, butyl-, pentyl-, hexyl-, benzyl-, phenyl-, and allyl esters of 2-hydroxyisobutyric acid; (ii) methyl-, ethyl-, propyl-, butyl-, pentyl-, hexyl-, benzyl-, phenyl-, and allyl esters of 2-hydroxy-2-methylbutyric acid; (iii) methyl-, ethyl-, propyl-, butyl-, pentyl-, hexyl-, benzyl-, phenyl-, and allyl esters of 2-hydroxy-2-ethylbutyric acid; (iv) methyl-, ethyl-, propyl-, butyl-, pentyl-, hexyl-, benzyl-, phenyl-, and allyl esters of lactic acid; and (v) methyl-, ethyl-, propyl-, butyl-, pentyl-, hexyl-, allyl-, benzyl-, and phenyl esters of glycolic acid. In some embodiments the quaternizing agent comprises methyl 2-hydroxyisobutyrate.

In some embodiments the quaternizing agent comprises an ester of a polycarboxylic acid. In this definition we mean to include dicarboxylic acids and carboxylic acids having more than 2 acidic moieties. In some embodiments the esters are alkyl esters with alkyl groups that contain from 1 to 4 carbon atoms. Suitable example include diesters of oxalic acid, diesters of phthalic acid, diesters of maleic acid, diesters of malonic acid or diesters or triesters of citric acid.

In some embodiments the quaternizing agent is an ester of a carboxylic acid having a pKa of less than 3.5. In such embodiments in which the compound includes more than one acid group, we mean to refer to the first dissociation constant. The quaternizing agent may be selected from an ester of a carboxylic acid selected from one or more of oxalic acid, phthalic acid, salicylic acid, maleic acid, malonic acid, citric acid, nitrobenzoic acid, aminobenzoic acid and 2, 4, 6-trihydroxybenzoic acid. In some embodiments the quaternizing agent includes dimethyl oxalate, a terephthalate, such as dimethyl terephthalate, and methyl 2-nitrobenzoate.

Quaternizing agents capable of coupling more than one quaternizable compound also may be employed. By "coupling" more than one quaternizable compounds, it is meant that at least two quaternizable compounds react with the same quaternizing agent to form a compound of the at least two quaternizable compounds linked by the quaternizing agent. Such quaternizing agents may, in some instances, also be referred to as coupling quaternizing agents herein and can include, for example, polyepoxides, such as, for example, di-, tri-, or higher epoxides; polyhalides; epoxy-halides, aromatic polyesters, and mixtures thereof.

In one embodiment, the quaternizing agent can be a polyepoxide. Polyepoxides can include, for example, polyglycidyls which can include, for example, di-epoxyoctane; ethylene glycol diglycidyl ether; neopentyl glycol digycidyl ether; 1,4-butanediol diglycidyl ether; 3(bis(glycidyl oxymethyl)-methoxy)-1,2-propanediol; 1,4-cyclohexane dimethanol digylicidyl ether; diepoxycyclo-octane, bisphenol A diglycidyl ether 4-vinyl-1-cyclohexene diepoxide; N,N-Diglycidyl-4-4glycidyloxyaniline; 1,6-hexane diglycidyl ether; trimethylolpropanetriglycidyl ether; polypropyleneglycol diglycidyl ether; polyepoxidized tri-glycerides, fats or oils; and mixtures thereof.

In one embodiment, the quaternizing agent may be derived from polyhalides, such as, for example, chlorides, iodides or bromides. Such polyhalides can include, but not be limited to, 1,5-dibromopentane; 1,4-diiodobutane; 1,5-dichloropentane; 1,12-dichlorododecane; 1,12-dibromododecane; 1,2-diiodoethane; 1,2-dibromoethane; and mixtures thereof.

In an embodiment, the quaternizing agent can be an epoxy-halide, such as, for example, epichlorohydrin and the like.

The quaternizing agent may also be a poly aromatic ester. Examples of poly aromatic esters can include, but not be limited to, 4,4'-oxybis(methylbenzoate); dimethylterephthalate; and mixtures thereof.

In certain embodiments the molar ratio of the quaternizable compound to quaternizing agent is 1:0.1 to 2, or 1:1 to 1.5, or 1:1 to 1.3. In some embodiments, particularly when employing a coupling quaternizing agent, the ratio of the quaternizable compound to the quaternizing agent can be from 2:1 to 1:1.

Any of the quaternizing agents described above, including the hydrocarbyl epoxides, may be used in combination with an acid. Suitable acids include carboxylic acids, such as acetic acid, propionic acid, 2-ethylhexanoic acid, and the like.

In some embodiments, the quaternizing agent can be employed in the presence of a protic solvent, such as, for example, 2-ethylhexanol, water, and combinations thereof. In some embodiments, the quaternizing agent can be employed in the presence of an acid. In yet another embodiment, the quaternizing agent can be employed in the presence of an acid and a protic solvent. In some embodiments, the acid can be an acid component in addition to the acid group present in the structure of the acylating agent. In further embodiments the reaction can be free of, or essentially free of, any additional acid component other than the acid group present in the structure of the acylating agent. By "free of" it is meant completely free, and by "essentially free" it is meant an amount that not materially affect the essential or basic and novel characteristics of the composition, such as, for example, less than 1% by weight.

Structure

While the process to prepare the quaternary ammonium salts can produce a mixture that is not readily definable apart from the process steps, certain structural components may be expected in some circumstances.

In some embodiments the quaternary ammonium salt can comprise, consist essentially of, or consist of a cation represented by the following formula:

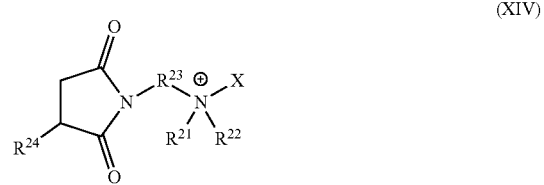

(XIV)

wherein: $R^{21}$ is a hydrocarbyl group containing from 1 to 10 carbon atoms; $R^{22}$ is a hydrocarbyl group containing from 1 to 10 carbon atoms; $R^{23}$ is a hydrocarbylene group containing from 1 to 20 carbon atoms; $R^{24}$ is a hydrocarbyl group containing less than 20 carbon atoms, or from 8 to 18, or from 12 to 18 carbon atoms; and X is a group derived from the quaternizing agent.

In some embodiments the quaternary ammonium salt can comprise, consist essentially of, or consist of a cation represented by the following formula:

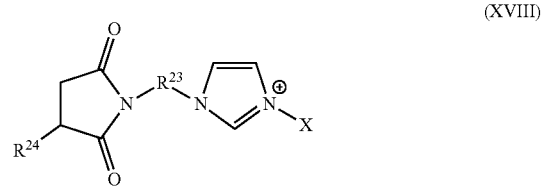

(XVIII)

wherein: $R^{23}$ is a hydrocarbylene group containing from 1 to 20 carbon atoms; $R^{24}$ is a hydrocarbyl group containing less than 20 carbon atoms, or from 8 to 18, or from 12 to 18 carbon atoms; and X is a group derived from the quaternizing agent.

In some embodiments the quaternary ammonium salt can comprise, consist essentially of, or consist of a coupled quaternary ammonium compound represented by the following formula:

(XIX)

wherein: Q and Q' are the same or different and represent quaternizable compounds, m and n are, individually, integers of between 1 and 4, and Xc represents a group derived from a coupling quaternizing agent, such as, for example, 1,4-butanediol diglycidyl ether, or bisphenol A diglycidyl ether. Exemplary coupled quaternary ammonium compounds can include, for example, any of the formulas below:

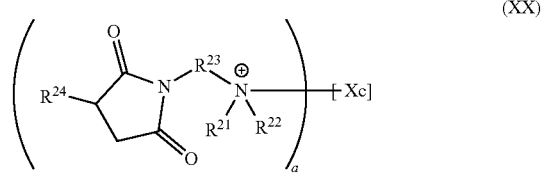

(XX)

where a is an integer of from 2 to 8. An example of formula XX where a is 2 or 3 can be represented, for example by formula XX' and XX" respectively;

(XX')

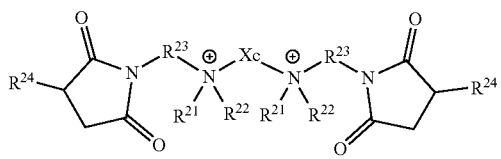

(XX")

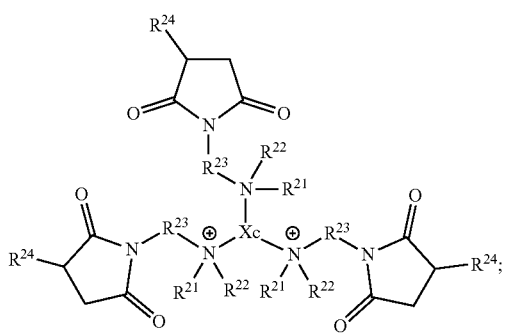

Even further example coupled quaternary ammonium compounds can be, for example, as provided in formulas XXIV below:

(XXIV)

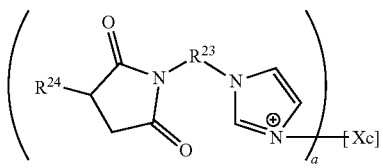

where a is an integer of from 2 to 8. An example of formula XXIV where a is 2 or 3 can be represented, for example by formula XXIV' and XXIV", respectively;

(XXIV')

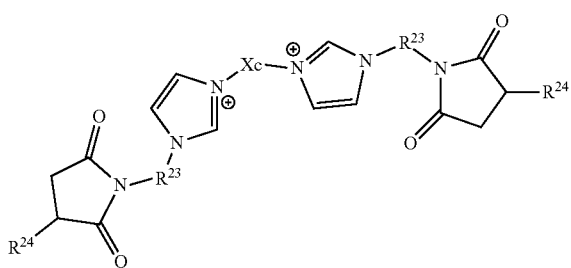

(XXIV")

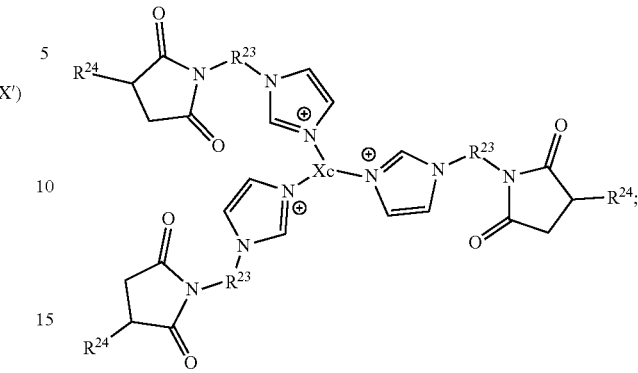

all wherein: $R^{21}$ through $R^{24}$ and Xc are as described above.

Compositions

In other embodiments, the present technology provides a composition comprising an imide containing quaternary ammonium salt, and the use of the composition in a fuel. In another embodiment, the present technology provides a composition comprising an imide containing quaternary ammonium salt, and the use of the composition in a lubricating composition with an oil of lubricating viscosity.

Fuel

The compositions of the present invention can comprise a fuel which is liquid at room temperature and is useful in fueling an engine. The fuel is normally a liquid at ambient conditions e.g., room temperature (20 to 30° C.). The fuel can be a hydrocarbon fuel, a nonhydrocarbon fuel, or a mixture thereof. The hydrocarbon fuel can be a petroleum distillate to include a gasoline as defined by EN228 or ASTM specification D4814, or a diesel fuel as defined by EN590 or ASTM specification D975. In an embodiment of the invention the fuel is a gasoline, and in other embodiments the fuel is a leaded gasoline, or a nonleaded gasoline. In another embodiment of this invention the fuel is a diesel fuel. The hydrocarbon fuel can be a hydrocarbon prepared by a gas to liquid process to include for example hydrocarbons prepared by a process such as the Fischer-Tropsch process. The nonhydrocarbon fuel can be an oxygen containing composition, often referred to as an oxygenate, to include an alcohol, an ether, a ketone, an ester of a carboxylic acid, a nitroalkane, or a mixture thereof. The nonhydrocarbon fuel can include for example methanol, ethanol, methyl t-butyl ether, methyl ethyl ketone, transesterified oils and/or fats from plants and animals such as rapeseed methyl ester and soybean methyl ester, and nitromethane. Mixtures of hydrocarbon and nonhydrocarbon fuels can include for example gasoline and methanol and/or ethanol, diesel fuel and ethanol, and diesel fuel and a transesterified plant oil such as rapeseed methyl ester. In an embodiment of the invention the liquid fuel is an emulsion of water in a hydrocarbon fuel, a nonhydrocarbon fuel, or a mixture thereof. In several embodiments of this invention the fuel can have a sulfur content on a weight basis that is 5000 ppm or less, 1000 ppm or less, 300 ppm or less, 200 ppm or less, 30 ppm or less, or 10 ppm or less. In another embodiment the fuel can have a sulfur content on a weight basis of 1 to 100 ppm. In one embodiment the fuel contains 0 ppm to 1000 ppm, or 0 to 500 ppm, or 0 to 100 ppm, or 0 to 50 ppm, or 0 to 25 ppm, or 0 to 10 ppm, or 0 to 5 ppm of alkali metals, alkaline earth metals, transition metals or mixtures thereof. In another embodiment the fuel contains 1 to 10 ppm by weight of alkali metals, alkaline earth metals, transition metals or mixtures thereof. It is well known in the art that a fuel containing alkali metals, alkaline earth metals, transition metals or mixtures thereof have a greater tendency to form deposits and therefore foul or plug common rail injectors. The fuel of the invention is present in a fuel composition in a major amount that is generally greater than 50 percent by weight, and in other embodiments is present at greater than 90 percent by weight, greater than 95 percent by weight, greater than 99.5 percent by weight, or greater than 99.8 percent by weight.

Treat rates of the composition comprising an imide containing quaternary ammonium salt with a number average molecular weight of 300-750 ("imide quat") to fuel range from 5 to 1000 ppm by a total weight of the fuel, or 5 to 500 ppm, or 10 to 250 ppm, or 10 to 150 ppm, or 15 to 100 ppm. In other embodiments the treat rate range may be from 250 to 1000 ppm, or 250 to 750 ppm, or 500 to 750 ppm or 250 ppm to 500 ppm.

Oil of Lubricating Viscosity

In lubricating composition embodiments, the compositions of the present invention can comprise an oil of lubricating viscosity. Such oils include natural and synthetic oils, oil derived from hydrocracking, hydrogenation, and hydrofinishing, unrefined, refined, re-refined oils or mixtures thereof. A more detailed description of unrefined, refined and re-refined oils is provided in International Publication WO2008/147704, paragraphs [0054] to [0056]. A more detailed description of natural and synthetic lubricating oils is provided in paragraphs [0058] to [0059] respectively of WO2008/147704. Synthetic oils may also be produced by Fischer-Tropsch reactions and typically may be hydroisomerized Fischer-Tropsch hydrocarbons or waxes. In one embodiment oils may be prepared by a Fischer-Tropsch gas-to liquid synthetic procedure as well as other gas-to-liquid oils.

Oils of lubricating viscosity may also be selected from any of the base oils in Groups I-V as specified in the American Petroleum Institute (API) Base Oil Interchangeability Guidelines. The five base oil groups are as follow; Group I: >0.03% sulfur or <90% saturates and viscosity index 80-120; Group II: <0.03% sulfur and ≥90% saturates and viscosity index 80-120; Group III: <0.03% sulfur and ≥90% saturates and viscosity index ≥120; Group IV: all polyalphaolefins; Group V: all others. Groups I, II and III are typically referred to as mineral oil base stocks.

Typical treat rates of the composition comprising an imide containing quaternary ammonium salt with a number average molecular weight of 300-750 ("imide quat") to lubricating oils is 0.1 to 10 wt % based on a total weight of the lubricating oil, or 0.5 to 5 wt % or 0.5 to 2.5 wt % or 0.5 to 1 wt % or 0.1 to 0.5 wt % or 1 to 2 wt %.

The amount of the oil of lubricating viscosity present is typically the balance remaining after subtracting from 100 wt % the sum of the amount of the compound of the invention and the other performance additives.

The lubricating composition may be in the form of a concentrate and/or fully formulated lubricant. If the lubricating composition of the invention (comprising the additives disclosed herein) is in the form of a concentrate which may be combined with additional oil to from, in whole or in part, a finished lubricant), the ratio of the of these additive to the oil of lubricating viscosity and/or diluent oil include the ranged of 1:99 to 99:1 by weight, or 80:20 to 10:90 by weight.

Miscellaneous

The fuel and/or lubricant compositions of the present invention include the imide quats described above and may also include one or more additional additives. Such additional performance additives can be added to any of the compositions described depending on the results desired and the application in which the composition will be used.

Although any of the additional performance additives described herein can be used in any of the fuel and/or lubricant compositions of the invention, the following additional additives are particularly useful for fuel and/or lubricant compositions: antioxidants, corrosion inhibitors, detergent and/or dispersant additives other than those described above, cold flow improvers, foam inhibitors, demulsifiers, lubricity agents, metal deactivators, valve seat recession additives, biocides, antistatic agents, deicers, fluidizers, combustion improvers, seal swelling agents, wax control polymers, scale inhibitors, gas-hydrate inhibitors, or any combination thereof.

In another embodiment, the present technology provides for more stable additive packages requiring less stabilizing solvent. These additive packages require less stabilizing solvent than additive packages comprising imide quats made with hydrocarbyl-substituted acylating agents having higher number average molecular weights (MW), such as greater than 300, or 550 or 1000. These stable additive packages may comprise one or more of the additives mentioned above and further described herein below.

Demulsifiers suitable for use with the imide quats of the present technology can include, but not be limited to, arylsulfonates and polyalkoxylated alcohol, such as, for example, polyethylene and polypropylene oxide copolymers and the like. The demulsifiers can also comprise nitrogen containing compounds such as oxazoline and imidazoline compounds and fatty amines, as well as Mannich compounds. Mannich compounds are the reaction products of alkylphenols and aldehydes (especially formaldehyde) and amines (especially amine condensates and polyalkylenepolyamines). The materials described in the following U.S. Patents are illustrative: U.S. Pat. Nos. 3,036,003; 3,236,770; 3,414,347; 3,448,047; 3,461,172; 3,539,633; 3,586,629; 3,591,598; 3,634,515; 3,725,480; 3,726,882; and 3,980,569 herein incorporated by reference. Other suitable demulsifiers are, for example, the alkali metal or alkaline earth metal salts of alkyl-substituted phenol- and naphthalenesulfonates and the alkali metal or alkaline earth metal salts of fatty acids, and also neutral compounds such as alcohol alkoxylates, e.g. alcohol ethoxylates, phenol alkoxylates, e.g. tert-butylphenol ethoxylate or tert-pentylphenol ethoxylate, fatty acids, alkylphenols, condensation products of ethylene oxide (EO) and propylene oxide (PO), for example including in the form of EO/PO block copolymers, polyethyleneimines or else polysiloxanes. Any of the commercially available demulsifiers may be employed, suitably in an amount sufficient to provide a treat level of from 5 to 50 ppm in the fuel. In an embodiment there is no demulsifier present in the fuel and/or lubricant composition. The demulsifiers may be used alone or in combination. Some demulsifiers are commercially available, for example from Nalco or Baker Hughes.

Suitable antioxidants include for example hindered phenols or derivatives thereof and/or diarylamines or derivatives thereof. Suitable detergent/dispersant additives include for example polyetheramines or nitrogen containing detergents, including but not limited to PIB amine detergents/dispersants, succinimide detergents/dispersants, and other quaternary salt detergents/dispersants including polyisobutylsuccinimide-derived quaternized PIB/amine and/or amide dispersants/detergents. Suitable cold flow improvers include for example esterified copolymers of maleic anhydride and styrene and/or copolymers of ethylene and vinyl acetate. Suitable lubricity improvers or friction modifiers are based typically on fatty acids or fatty acid esters. Typical examples are tall oil fatty acid, as described, for example, in WO 98/004656, and glyceryl monooleate. The reaction products, described in U.S. Pat. No. 6,743,266 B2, of natural or synthetic oils, for example triglycerides, and alkanolamines are also suitable as such lubricity improvers. Additional examples include commercial tall oil fatty acids containing polycyclic hydrocarbons and/or rosin acids.

Suitable metal deactivators include for example aromatic triazoles or derivatives thereof, including but not limited to benzotriazole. Other suitable metal deactivators are, for example, salicylic acid derivatives such as N,N'-disalicylidene-1,2-propanediamine. Suitable valve seat recession additives include for example alkali metal sulfosuccinate salts. Suitable foam inhibitors and/or antifoams include for example organic silicones such as polydimethyl siloxane, polyethylsiloxane, polydiethylsiloxane, polyacrylates and polymethacrylates, trimethyl-triflouro-propylmethyl siloxane and the like. Suitable fluidizers include for example mineral oils and/or poly(alpha-olefins) and/or polyethers. Combustion improvers include for example octane and cetane improvers. Suitable cetane number improvers are, for example, aliphatic nitrates such as 2-ethylhexyl nitrate and cyclohexyl nitrate and peroxides such as di-tert-butyl peroxide.

The additional performance additives, which may be present in the fuel and/or lubricant compositions of the invention, also include di-ester, di-amide, ester-amide, and ester-imide friction modifiers prepared by reacting an α-hydroxy acid with an amine and/or alcohol optionally in the presence of a known esterification catalyst. Examples of α-hydroxy acids include glycolic acid, lactic acid, α-hydroxy dicarboxylic acid (such as tartaric acid) and/or an α-hydroxy tricarboxylic acid (such as citric acid), with an amine and/or alcohol, optionally in the presence of a known esterification catalyst. These friction modifiers, often derived from tartaric acid, citric acid, or derivatives thereof, may be derived from amines and/or alcohols that are branched, resulting in friction modifiers that themselves have significant amounts of branched hydrocarbyl groups present within it structure. Examples of suitable branched alcohols used to prepare such friction modifiers include 2-ethylhexanol, isotridecanol, Guerbet alcohols, and mixtures thereof. Friction modifiers may be present at 0 to 6 wt % or 0.001 to 4 wt %, or 0.01 to 2 wt % or 0.05 to 3 wt % or 0.1 to 2 wt % or 0.1 to 1 wt % or 0.001 to 0.01 wt %.

The additional performance additives may comprise a detergent/dispersant comprising a hydrocarbyl substituted acylating agent. The acylating agent may be, for example, a hydrocarbyl substituted succinic acid, or the condensation product of a hydrocarbyl substituted succinic acid with an amine or an alcohol; that is, a hydrocarbyl substituted succinimide or hydrocarbyl substituted succinate. In an embodiment, the detergent/dispersant may be a polyisobutenyl substituted succinic acid, amide or ester, wherein the polyisobutenyl substituent has a number average molecular weight of 100 to 5000. In some embodiments, the detergent may be a C6 to C18 substituted succinic acid, amide or ester. A more thorough description of the hydrocarbyl substituted acylating agent detergents can be found from paragraph [0017] to [0036] of U.S. Publication 2011/0219674, published Sep. 15, 2011.

In one embodiment, the additional detergent/dispersant may be quaternary ammoniums salts other than that of the present technology. The additional quaternary ammoniums salts can be quaternary ammoniums salts prepared from hydrocarbyl substituted acylating agents, such as, for example, polyisobutyl succinic acids or anhydrides, having a hydrocarbyl substituent with a number average molecular weight of greater than 1200 $M_n$, polyisobutyl succinic acids or anhydrides, having a hydrocarbyl substituent with a number average molecular weight of 300 to 750, or polyisobutyl succinic acids anhydrides, having a hydrocarbyl substituent with a number average molecular weight of 1000 $M_n$.

In an embodiment, the additional quaternary ammonium salts prepared from the reaction of nitrogen containing compound and a hydrocarbyl substituted acylating agent having a hydrocarbyl substituent with a number average molecular weight of 1300 to 3000 is an imide. In an embodiment, the quaternary ammonium salts prepared from the reaction of nitrogen containing compound and a hydrocarbyl substituted acylating agent having a hydrocarbyl substituent with a number average molecular weight of greater than 1200 $M_n$ or having a hydrocarbyl substituent with a number average molecular weight of 300 to 750 is an amide or ester.

In yet another embodiment the hydrocarbyl substituted acylating agent can include a mono-, dimer or trimer carboxylic acid with 8 to 54 carbon atoms and is reactive with primary or secondary amines. Suitable acids include, but are not limited to, the mono-, dimer, or trimer acids of caprylic acid, capric acid, lauric acid, myristic acid, palmitic acid, stearic, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid.

The hydrocarbyl substituted acylating agent may also be a copolymer formed by copolymerizing at least one monomer that is an ethylenically unsaturated hydrocarbon having 2 to 100 carbon atoms. The monomer may be linear, branched, or cyclic. The monomer may have oxygen or nitrogen substituents, but will not react with amines or alcohols. The monomer may be reacted with a second monomer that is a carboxylic acid or carboxylic acid derivative having 3 to 12 carbon atoms. The second monomer may have one or two carboxylic acid functional groups and is reactive with amines or alcohols. When made using this process, the hydrocarbyl substituted acylating agent copolymer has a number average molecular weight $M_n$ of 500 to 20,000.

Alternatively, the hydrocarbyl substituted acylating agent may be a terpolymer that is the reaction product of ethylene and at least one monomer that is an ethylenically unsaturated monomer having at least one tertiary nitrogen atom, with (i) an alkenyl ester of one or more aliphatic monocarboxylic acids having 1 to 24 carbon atoms or (ii) an alkyl ester of acrylic or methacrylic acid.

In an embodiment the nitrogen containing compound of the additional quaternary ammonium salts is an imidazole or nitrogen containing compound of either of formulas.

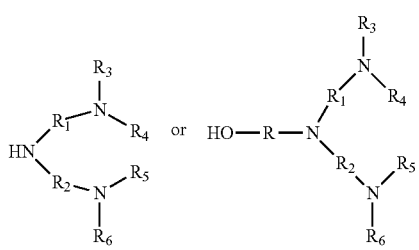

wherein R may be a $C_1$ to $C_6$ alkylene group; each of $R_1$ and $R_2$, individually, may be a $C_1$ to $C_6$ hydrocarbylene group; and each of $R_3$, $R_4$, $R_5$, and $R_6$, individually, may be a hydrogen or a $C_1$ to $C_6$ hydrocarbyl group. In one embodiment $R_1$ or $R_2$ can be, for example, a $C_1$, $C_2$ or $C_3$ alkylene group. In the same or different embodiments, each $R_3$, $R_4$, $R_5$, $R_6$ can be, for example, H or a $C_1$, $C_2$ or $C_3$ alkyl group.

In other embodiments, the quaternizing agent used to prepare the additional quaternary ammonium salts can be a dialkyl sulfate, an alkyl halide, a hydrocarbyl substituted carbonate, a hydrocarbyl epoxide, a carboxylate, alkyl esters, or mixtures thereof. In some cases the quaternizing agent can be a hydrocarbyl epoxide. In some cases the quaternizing agent can be a hydrocarbyl epoxide in combination with an acid. In some cases the quaternizing agent can be a salicylate, oxalate or terephthalate. In an embodiment the hydrocarbyl epoxide may be an alcohol functionalized epoxide or $C_4$ to $C_{14}$ epoxide. In yet another embodiment, the hydrocarbyl epoxide may be an alcohol functionalized epoxide or $C_4$ to $C_{20}$ epoxide.

In some embodiments, the quaternizing agent is multifunctional resulting in the additional quaternary ammonium salts being a coupled quaternary ammoniums salts.

Additional quaternary ammonium salts include, but are not limited to quaternary ammonium salts having a hydrophobic moiety in the anion. Exemplary compounds include quaternary ammonium compounds having the formula below:

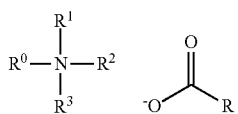

wherein $R^0$, $R^1$, $R^2$ and $R^3$ is each individually an optionally substituted alkyl, alkenyl or aryl group and R includes an optionally substituted hydrocarbyl moiety having at least 5 carbon atoms.

Additional quaternary ammonium salts may also include polyetheramines that are the reaction products of a polyether-substituted amine comprising at least one tertiary quaternizable amino group and a quaternizing agent that converts the tertiary amino group to a quaternary ammonium group.

Dispersants can also be post-treated by reaction with any of a variety of agents. Among these are urea, thiourea, dimercaptothiadiazoles, carbon disulfide, aldehydes, ketones, carboxylic acids, hydrocarbon-substituted succinic anhydrides, nitriles, epoxides, boron compounds, and phosphorus compounds. References detailing such treatment are listed in U.S. Pat. No. 4,654,403.

In yet other embodiments, the compostions may further comprise a hydrolized succinic acid or anhydride. The hydrolized succinic acid or anhydride may have a $M_n$ ranging from 225 to 1000. In another embodiment, the hydrolized succinic acid or anhydride may have a $M_n$ of 1000 and more than 70 mole % vinylidene groups ("high-vinylidene"). In another embodiment, the hydrolized succinic acid or anhydride may have a $M_n$ of 550 and between 20 mole % and 70 mole % vinylidene groups ("mid-vinylidene"). In yet other embodiments the hydrolized succinic acid or anhydride may have a $M_n$ of less than 550 and less than 20 mole % vinylidene groups ("conventional vinylidene").

The fuel and/or lubricant compositions of the invention may include a detergent additive different from the imide quat technology. Most conventional detergents used in the field of engine lubrication obtain most or all of their basicity or TBN from the presence of basic metal-containing compounds (metal hydroxides, oxides, or carbonates, typically based on such metals as calcium, magnesium, or sodium). Such metallic overbased detergents, also referred to as overbased or superbased salts, are generally single phase, homogeneous Newtonian systems characterized by a metal content in excess of that which would be present for neutralization according to the stoichiometry of the metal and the particular acidic organic compound reacted with the metal. The overbased materials are typically prepared by reacting an acidic material (typically an inorganic acid or lower carboxylic acid such as carbon dioxide) with a mixture of an acidic organic compound (also referred to as a substrate), a stoichiometric excess of a metal base, typically in a reaction medium of an one inert, organic solvent (e.g., mineral oil, naphtha, toluene, xylene) for the acidic organic substrate. Typically also a small amount of promoter such as a phenol or alcohol is present, and in some cases a small amount of water. The acidic organic substrate will normally have a sufficient number of carbon atoms to provide a degree of solubility in oil.

Such conventional overbased materials and their methods of preparation are well known to those skilled in the art. Patents describing techniques for making basic metallic salts of sulfonic acids, carboxylic acids, phenols, phosphonic acids, and mixtures of any two or more of these include U.S. Pat. Nos. 2,501,731; 2,616,905; 2,616,911; 2,616,925; 2,777,874; 3,256,186; 3,384,585; 3,365,396; 3,320,162; 3,318,809; 3,488,284; and 3,629,109. Salixarate detergents are described in U.S. Pat. No. 6,200,936. In certain embodiments, the detergent may contain a metal-containing salicylate detergent, such as an overbased calcium hydrocarbyl-substituted salicylate detergent and are described in U.S. Pat. Nos. 5,688,751 and 4,627,928.

Viscosity improvers (also sometimes referred to as viscosity index improvers or viscosity modifiers) may be included in the fuel and/or lubricant compositions of this invention. Viscosity improvers are usually polymers, including polyisobutenes, polymethacrylates (PMA) and polymethacrylic acid esters, hydrogenated diene polymers, polyalkylstyrenes, esterified styrene-maleic anhydride copolymers, hydrogenated alkenylarene-conjugated diene copolymers and polyolefins. PMA's are prepared from mixtures of methacrylate monomers having different alkyl groups. The alkyl groups may be either straight chain or branched chain groups containing from 1 to 18 carbon atoms. Most PMA's are viscosity modifiers as well as pour point depressants.

Multifunctional viscosity improvers, which also have dispersant and/or antioxidancy properties are known and may optionally be used in the fuel and/or lubricant compositions. Dispersant viscosity modifiers (DVM) are one example of such multifunctional additives. DVM are typically prepared by copolymerizing a small amount of a nitrogen-containing monomer with alkyl methacrylates, resulting in an additive with some combination of dispersancy, viscosity modification, pour point depressancy and dispersancy. Vinyl pyridine, N-vinyl pyrrolidone and N,N'-dimethylaminoethyl methacrylate are examples of nitrogen-containing monomers. Polyacrylates obtained from the polymerization or copolymerization of one or more alkyl acrylates also are useful as viscosity modifiers.

Anti-wear agents may be used in the fuel and/or lubricant compositions provide herein. Anti-wear agents can in some embodiments include phosphorus-containing antiwear/extreme pressure agents such as metal thiophosphates, phosphoric acid esters and salts thereof, phosphorus-containing carboxylic acids, esters, ethers, and amides; and phosphites. In certain embodiments a phosphorus antiwear agent may be present in an amount to deliver 0.01 to 0.2 or 0.015 to 0.15 or 0.02 to 0.1 or 0.025 to 0.08 percent by weight phosphorus. Often the antiwear agent is a zinc dialkyldithiophosphate (ZDP). For a typical ZDP, which may contain 11 percent P (calculated on an oil free basis), suitable amounts may include 0.09 to 0.82 percent by weight. Non-phosphorus-containing anti-wear agents include borate esters (including borated epoxides), dithiocarbamate compounds, molybdenum-containing compounds, and sulfurized olefins. In some embodiments the fuel and/or lubricant compositions of the invention are free of phosphorus-containing antiwear/extreme pressure agents.

Foam inhibitors that may be useful in fuel and/or lubricant compositions of the invention include polysiloxanes, copolymers of ethyl acrylate and 2-ethylhexylacrylate and optionally vinyl acetate; demulsifiers including fluorinated polysiloxanes, trialkyl phosphates, polyethylene glycols, polyethylene oxides, polypropylene oxides and (ethylene oxide-propylene oxide) polymers. The disclosed technology may also be used with a silicone-containing antifoam agent in combination with a $C_5$-$C_{17}$ alcohol.

Pour point depressants that may be useful in fuel and/or lubricant compositions of the invention include polyalphaolefins, esters of maleic anhydride-styrene copolymers, poly(meth)acrylates, polyacrylates or polyacrylamides.

Metal deactivators may be chosen from a derivative of benzotriazole (typically tolyltriazole), 1,2,4-triazole, benzimidazole, 2-alkyldithiobenzimidazole or 2-alkyldithiobenzothiazole, 1-amino-2-propanol, a derivative of dimercaptothiadiazole, octylamine octanoate, condensation products of dodecenyl succinic acid or anhydride and/or a fatty acid such as oleic acid with a polyamine. The metal deactivators may also be described as corrosion inhibitors.

Seal swell agents include sulpholene derivatives Exxon Necton-37™ (FN 1380) and Exxon Mineral Seal Oil™ (FN 3200).

Exemplary additive package compositions are included in Table 1. The amounts shown are in weight percents, based on a total weight of the additive package.

TABLE 1

| | Additive Package A | Additive Package B | Additive Package C | Additive Package D | Additive Package E |
|---|---|---|---|---|---|
| Imide Quat | 5 to 20 | 10 to 30 | 10 to 30 | 10 to 30 | 30 to 45 |
| Hydrolyzed PIBSA | 10 to 20 | 5 to 15 | 5 to 15 | 5 to 15 | 10 to 20 |
| Commercial demulsifier | 1 to 2 | 2 to 6 | 2 to 6 | 2 to 4 | 1 to 2 |
| Polydimethyl siloxane foam inhibitor | 0.5 to 1.5 | 1 to 3 | 2 to 3 | 0.5 to 1 | 0 |
| Aromatic 150 solvent | 50 to 70 | 60 to 80 | 60 to 80 | 55 to 70 | 30 to 40 |
| Ethyl hexyl alcohol | 5 to 20 | 0 | 0 | 5 to 10 | 10 to 20 |

Fuel Compositions

In some embodiments the technology provides fuel compositions. In some embodiments, the fuel compositions comprise a majority (>50 wt %) of gasoline or a middle distillate fuel. In an embodiment, there is provided a fuel composition comprising a majority of a diesel fuel.

In a yet another embodiment, the fuel composition comprises the imide quats of the disclosed technology as described above and at least one demulsifier. Demulsifiers suitable for use with the quaternary ammonium salts of the present technology can include, but not be limited to arylsulfonates and polyalkoxylated alcohol, such as, for example, polyethylene and polypropylene oxide copolymers and the like. The demulsifiers can also comprise nitrogen containing compounds such as oxazoline and imidazoline compounds and fatty amines, as well as Mannich compounds. Mannich compounds are the reaction products of alkylphenols and aldehydes (especially formaldehyde) and amines (especially amine condensates and polyalkylenepolyamines). The materials described in the following U.S. Patents are illustrative: U.S. Pat. Nos. 3,036,003; 3,236,770; 3,414,347; 3,448,047; 3,461,172; 3,539,633; 3,586,629; 3,591,598; 3,634,515; 3,725,480; 3,726,882; and 3,980,569 herein incorporated by reference. Other suitable demulsifiers are, for example, the alkali metal or alkaline earth metal salts of alkyl-substituted phenol- and naphthalenesulfonates and the alkali metal or alkaline earth metal salts of fatty acids, and also neutral compounds such as alcohol alkoxylates, e.g. alcohol ethoxylates, phenol alkoxylates, e.g. tert-butylphenol ethoxylate or tert-pentylphenol ethoxylate, fatty acids, alkylphenols, condensation products of ethylene oxide (EO) and propylene oxide (PO), for example including in the form of EO/PO block copolymers, polyethyleneimines or else polysiloxanes. Any of the commercially available demulsifiers may be employed, suitably in an amount sufficient to provide a treat level of from 5 to 50 ppm in the fuel. In one embodiment the fuel composition of the invention does not comprise a demulsifier. The demulsifiers may be used alone or in combination. Some demulsifiers are commercially available, for example from Nalco or Baker Hughes. Typical treat rates of the demulsifiers to a fuel may range from 0 to 50 ppm by total weight of the fuel, or 5 to 50 ppm, or 5 to 25 ppm, or 5 to 20 ppm.

The disclosed technology may also be used with demulsifiers comprising a hydrocarbyl-substituted dicarboxylic acid in the form of the free acid, or in the form of the anhydride which may be an intramolecular anhydride, such as succinic, glutaric, or phthalic anhydride, or an intermolecular anhydride linking two dicarboxylic acid molecules together. The hydrocarbyl substituent may have from 12 to 2000 carbon atoms and may include polyisobutenyl substituents having a number average molecular weight of 300 to 2800. Exemplary hydrocarbyl-substituted dicarboxylic acids include, but are not limited to, hydrocarbyl-substituted acids derived from malonic, succinic, glutaric, adipic, pimelic, suberic, azelaic, sebacic, undecanedioic, dodecanedioic, phthalic, isophthalic, terphthalic, o-, m-, or p-phenylene diacetic, maleic, fumaric, or glutaconic acids.

In another embodiment, a fuel composition comprises the imide quats of the disclosed technology and an additional detergent/dispersant. Customary detergent/dispersant additives are preferably amphiphilic substances which possess at least one hydrophobic hydrocarbon radical with a number average molecular weight of 100 to 10000 and at least one polar moiety selected from (i) Mono- or polyamino groups having up to 6 nitrogen atoms, at least one nitrogen atom having basic properties; (ii) Hydroxyl groups in combination with mono or polyamino groups, at least one nitrogen atoms having basic properties; (iii) Carboxyl groups or their alkali metal or alkaline earth metal salts; (iv) Sulfonic acid groups or their alkali metal or alkaline earth metal salts; (v) Poly-oxy-$C_2$ to $C_4$ alkylene moieties terminated by hydroxyl groups, mono- or polyamino groups, at least one nitrogen atom having basic properties, or by carbamate groups; (vi) Carboxylic ester groups; (vii) Moieties derived from succinic anhydride and having hydroxyl and/or amino and/or amido and/or imido groups; and/or (viii) Moieties obtained by Mannich reaction of substituted phenols with aldehydes and mono- or polyamines.

The hydrophobic hydrocarbon radical in the above detergent/dispersant additives which ensures the adequate solubility in the fuel, has a number average molecular weight ($M_n$) of 85 to 20,000, of 1113 to 10,000, or of 300 to 5000. In yet another embodiment, the detergent/dispersant additives have a $M_n$ of 300 to 3000, of 500 to 2500, of 700 to 2500, or 800 to 1500. Typical hydrophobic hydrocarbon radicals, may be polypropenyl, polybutenyl and polyisobutenyl radicals, with a number average molecular weight $M_n$, of 300 to 5000, of 300 to 3000, of 500 to 2500, or 700 to 2500. In one embodiment the detergent/dispersant additives have a $M_n$ of 800 to 1500.

The additional performance additives may comprise a high TBN nitrogen containing detergent/dispersant, such as a succinimide, that is the condensation product of a hydrocarbyl-substituted succinic anhydride with a poly(alkyleneamine). Succinimide detergents/dispersants are more fully described in U.S. Pat. Nos. 4,234,435 and 3,172,892. Another class of ashless dispersant is high molecular weight esters, prepared by reaction of a hydrocarbyl acylating agent and a polyhydric aliphatic alcohol such as glycerol, pentaerythritol, or sorbitol. Such materials are described in more detail in U.S. Pat. No. 3,381,022.

Nitrogen-containing detergents may be the reaction products of a carboxylic acid-derived acylating agent and an amine. The acylating agent can vary from formic acid and its acylating derivatives to acylating agents having high molecular weight aliphatic substituents of up to 5,000, 10,000 or 20,000 carbon atoms. The amino compounds can vary from ammonia itself to amines typically having aliphatic substituents of up to 30 carbon atoms, and up to 11 nitrogen atoms. Acylated amino compounds suitable for use in the present invention may be those formed by the reaction of an acylating agent having a hydrocarbyl substituent of at least 8 carbon atoms and a compound comprising at least one primary or secondary amine group. The acylating agent may be a mono- or polycarboxylic acid (or reactive equivalent thereof) for example a substituted succinic, phthalic or propionic acid and the amino compound may be a polyamine or a mixture of polyamines, for example a mixture of ethylene polyamines. Alternatively the amine may be a hydroxyalkyl-substituted polyamine. The hydrocarbyl substituent in such acylating agents may comprise at least 10 carbon atoms. In one embodiment, the hydrocarbyl substituent may comprise at least 12, for example 30 or 50 carbon atoms. In yet another embodiment, it may comprise up to 200 carbon atoms. The hydrocarbyl substituent of the acylating agent may have a number average molecular weight ($M_n$) of 170 to 2800, for example from 250 to 1500. In other embodiments, the substituent's $M_n$ may range from 500 to 1500, or alternatively from 500 to 1100. In yet another embodiment, the substituent's $M_n$ may range from 700 to 1300. In another embodiment, the hydrocarbyl substituent may have a number average molecular weight of 700 to 1000, or 700 to 850, or, for example, 750.

Another class of ashless dispersant is Mannich bases. These are materials which are formed by the condensation of a higher molecular weight, alkyl substituted phenol, an alkylene polyamine, and an aldehyde such as formaldehyde and are described in more detail in U.S. Pat. No. 3,634,515.

A useful nitrogen containing dispersant includes the product of a Mannich reaction between (a) an aldehyde, (b) a polyamine, and (c) an optionally substituted phenol. The phenol may be substituted such that the Mannich product has a molecular weight of less than 7500. Optionally, the molecular weight may be less than 2000, less than 1500, less than 1300, or for example, less than 1200, less than 1100, less than 1000. In some embodiments, the Mannich product has a molecular weight of less than 900, less than 850, or less than 800, less than 500, or less than 400. The substituted phenol may be substituted with up to 4 groups on the aromatic ring. For example it may be a tri or di-substituted phenol. In some embodiments, the phenol may be a mono-substituted phenol. The substitution may be at the ortho, and/or meta, and/or para position(s). To form the Mannich product, the molar ratio of the aldehyde to amine is from 4:1 to 1:1 or, from 2:1 to 1:1. The molar ratio of the aldehyde to phenol may be at least 0.75:1; preferably from 0.75 to 1 to 4:1, preferably 1:1 to 4;1 more preferably from 1:1 to 2:1. To form the preferred Mannich product, the molar ratio of the phenol to amine is preferably at least 1.5:1, more preferably at least 1.6:1, more preferably at least 1.7:1, for example at least 1.8:1, preferably at least 1.9:1. The molar ratio of phenol to amine may be up to 5:1; for example it may be up to 4:1, or up to 3.5:1. Suitably it is up to 3.25:1, up to 3:1, up to 2.5:1, up to 2.3:1 or up to 2.1:1.

Other dispersants include polymeric dispersant additives, which are generally hydrocarbon-based polymers which contain polar functionality to impart dispersancy characteristics to the polymer. An amine is typically employed in preparing the high TBN nitrogen-containing dispersant. One or more poly(alkyleneamine)s may be used, and these may comprise one or more poly(ethyleneamine)s having 3 to 5 ethylene units and 4 to 6 nitrogen units. Such materials include triethylenetetramine (TETA), tetraethylenepentamine (TEPA), and pentaethylenehexamine (PEHA). Such materials are typically commercially available as mixtures of various isomers containing a range number of ethylene units and nitrogen atoms, as well as a variety of isomeric structures, including various cyclic structures. The poly(alkyleneamine) may likewise comprise relatively higher molecular weight amines known in the industry as ethylene amine still bottoms.

In an embodiment, the fuel composition can additionally comprise quaternary ammonium salts other than the imide quats described herein. The other quaternary ammonium salts can comprise (a) a compound comprising (i) at least one tertiary amino group as described above, and (ii) a hydrocarbyl-substituent having a number average molecular weight of 100 to 5000, or 250 to 4000, or 100 to 4000 or 100 to 2500 or 3000; and (b) a quaternizing agent suitable for converting the tertiary amino group of (a)(i) to a quaternary nitrogen, as described above. The other quaternary ammonium salts are more thoroughly described in U.S. Pat. No. 7,951,211, issued May 31, 2011, and U.S. Pat. No. 8,083,814, issued Dec. 27, 2011, and U.S. Publication Nos. 2013/0118062, published May 16, 2013, 2012/0010112, published Jan. 12, 2012, 2013/0133243, published May 30, 2013, 2008/0113890, published May 15, 2008, and 2011/0219674, published Sep. 15, 2011, US 2012/0149617 published May 14, 2012, US 2013/0225463 published Aug. 29, 2013, US 2011/0258917 published Oct. 27, 2011, US 2011/0315107 published Dec. 29, 2011, US 2013/0074794 published Mar. 28, 2013, US 2012/0255512 published Oct. 11, 2012, US 2013/0333649 published Dec. 19, 2013, US 2013/0118062 published May 16, 2013, and international publications WO Publication Nos. 2011/141731, published Nov. 17, 2011, 2011/095819, published Aug. 11, 2011, and 2013/017886, published Feb. 7, 2013, WO 2013/070503 published May 16, 2013, WO 2011/110860 published Sep. 15, 2011, WO 2013/017889 published Feb. 7, 2013, WO 2013/017884 published Feb. 7, 2013.

The additional quaternary ammoniums salts other than the invention can be quaternary ammoniums salts prepared from hydrocarbyl substituted acylating agents, such as, for example, polyisobutyl succinic acids or anhydrides, having a hydrocarbyl substituent with a number average molecular weight of greater than 1200 $M_n$, polyisobutyl succinic acids or anhydrides, having a hydrocarbyl substituent with a number average molecular weight of 300 to 750, or polyisobutyl succinic acids or anhydrides, having a hydrocarbyl substituent with a number average molecular weight of 1000 $M_n$.

In an embodiment, the fuel composition comprising the quaternary ammonium salts of this invention can further comprise additional quaternary ammonium salts. The additional salts may be an imide prepared from the reaction of a nitrogen containing compound and a hydrocarbyl substituted acylating agent having a hydrocarbyl substituent with a number average molecular weight of 1300 to 3000. In an embodiment, the quaternary ammonium salts prepared from the reaction of nitrogen containing compound and a hydrocarbyl substituted acylating agent having a hydrocarbyl substituent with a number average molecular weight of greater than 1200 $M_n$ or, having a hydrocarbyl substituent with a number average molecular weight of 300 to 750 is an amide or ester.

In an embodiment the nitrogen containing compound of the additional quaternary ammonium salts is an imidazole or nitrogen containing compound of either of formulas:

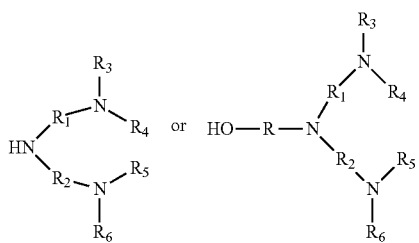

wherein R may be a $C_1$ to C alkylene group; each of $R_1$ and $R_2$, individually, may be a $C_1$ to $C_6$ hydrocarbylene group; and each of $R_3$, $R_4$, $R_5$, and $R_6$, individually, may be a hydrogen or a $C_1$ to $C_6$ hydrocarbyl group.

In other embodiments, the quaternizing agent used to prepare the additional quaternary ammonium salts can be a dialkyl sulfate, an alkyl halide, a hydrocarbyl substituted carbonate, a hydrocarbyl epoxide, a carboxylate, alkyl esters, or mixtures thereof. In some cases the quaternizing agent can be a hydrocarbyl epoxide. In some cases the quaternizing agent can be a hydrocarbyl epoxide in combination with an acid. In some cases the quaternizing agent can be a salicylate, oxalate or terephthalate. In an embodiment the hydrocarbyl epoxide is an alcohol functionalized epoxides or $C_4$ to $C_{14}$ epoxides.

In some embodiments, the quaternizing agent is multifunctional resulting in the additional quaternary ammonium salts being a coupled quaternary ammoniums salts.

Typical treat rates of additional detergents/dispersants to a fuel of the invention is 0 to 500 ppm, or 0 to 250 ppm, or 0 to 100 ppm, or 5 to 250 ppm, or 5 to 100 ppm, or 10 to 100 ppm.

In a particular embodiment, a fuel composition comprises the imide quats of the present technology and a cold flow improver. The cold flow improver is typically selected from (1) copolymers of a $C_2$- to $C_{40}$-olefin with at least one further ethylenically unsaturated monomer; (2) comb polymers; (3) polyoxyalkylenes; (4) polar nitrogen compounds; (5) sulfocarboxylic acids or sulfonic acids or derivatives thereof, and (6) poly(meth)acrylic esters. It is possible to use either mixtures of different representatives from one of the particular classes (1) to (6) or mixtures of representatives from different classes (1) to (6).

Suitable $C_2$- to $C_{40}$-olefin monomers for the copolymers of class (1) are, for example, those having 2 to 20 and especially 2 to 10 carbon atoms, and 1 to 3 and preferably 1 or 2 carbon-carbon double bonds, especially having one carbon-carbon double bond. In the latter case, the carbon-carbon double bond may be arranged either terminally (α-olefins) or internally. However, preference is given to α-olefins, more preferably α-olefins having 2 to 6 carbon atoms, for example propene, 1-butene, 1-pentene, 1-hexene and in particular ethylene. The at least one further ethylenically unsaturated monomer of class (1) is preferably selected from alkenyl carboxylates; for example, $C_2$- to $C_{14}$-alkenyl esters, for example the vinyl and propenyl esters, of carboxylic acids having 2 to 21 carbon atoms, whose hydrocarbon radical may be linear or branched among these, preference is given to the vinyl esters, examples of suitable alkenyl carboxylates are vinyl acetate, vinyl propionate, vinyl butyrate, vinyl 2-ethylhexanoate, vinyl neopentanoate, vinyl hexanoate, vinyl neononanoate, vinyl neodecanoate and the corresponding propenyl esters, (meth)acrylic esters; for example, esters of (meth)acrylic acid with $C_1$- to $C_{20}$-alkanols, especially $C_1$- to $C_{10}$-alkanols, in particular with methanol, ethanol, propanol, isopropanol, n-butanol, sec-butanol, isobutanol, tert-butanol, pentanol, hexanol, heptanol, octanol, 2-ethylhexanol, nonanol and decanol, and structural isomers thereof and further olefins; preferably higher in molecular weight than the abovementioned $C_2$- to $C_{40}$-olefin base monomer for example, the olefin base monomer used is ethylene or propene, suitable further olefins are in particular $C_{10}$- to $C_{40}$-α-olefins.

Suitable copolymers of class (1) are also those which comprise two or more different alkenyl carboxylates in copolymerized form, which differ in the alkenyl function and/or in the carboxylic acid group. Likewise suitable are copolymers which, as well as the alkenyl carboxylate(s), comprise at least one olefin and/or at least one (meth)acrylic ester in copolymerized form.

Terpolymers of a $C_2$- to $C_{40}$-α-olefin, a $C_1$- to $C_{20}$-alkyl ester of an ethylenically unsaturated monocarboxylic acid having 3 to 15 carbon atoms and a $C_2$- to $C_{14}$-alkenyl ester of a saturated monocarboxylic acid having 2 to 21 carbon atoms are also suitable as copolymers of class (K1). Terpolymers of this kind are described in WO 2005/054314. A typical terpolymer of this kind is formed from ethylene, 2-ethylhexyl acrylate and vinyl acetate.

The at least one or the further ethylenically unsaturated monomer(s) are copolymerized in the copolymers of class (1) in an amount of preferably 1 to 50% by weight, especially 10 to 45% by weight and in particular 20 to 40% by weight, based on the overall copolymer. The main proportion in terms of weight of the monomer units in the copolymers of class (1) therefore originates generally from the $C_2$ to $C_{40}$ base olefins. The copolymers of class (1) may have a number average molecular weight $M_n$ of 1000 to 20,000, or 1000 to 10,000 or 1000 to 8000.

Typical comb polymers of component (2) are, for example, obtainable by the copolymerization of maleic anhydride or fumaric acid with another ethylenically unsaturated monomer, for example with an α-olefin or an unsaturated ester, such as vinyl acetate, and subsequent esterification of the anhydride or acid function with an alcohol having at least 10 carbon atoms. Further suitable comb polymers are copolymers of α-olefins and esterified comonomers, for example esterified copolymers of styrene and maleic anhydride or esterified copolymers of styrene and fumaric acid. Suitable comb polymers may also be polyfumarates or polymaleates. Homo- and copolymers of vinyl ethers are also suitable comb polymers. Comb polymers suitable as components of class (2) are, for example, also those described in WO 2004/035715 and in "Comb-Like Polymers. Structure and Properties", N. A. Plate and V. P. Shibaev, J. Poly. Sci. Macromolecular Revs. 8, pages 117 to 253 (1974). Mixtures of comb polymers are also suitable.

Polyoxyalkylenes suitable as components of class (3) are, for example, polyoxyalkylene esters, polyoxyalkylene ethers, mixed polyoxyalkylene ester/ethers and mixtures thereof. These polyoxyalkylene compounds preferably comprise at least one linear alkyl group, preferably at least two linear alkyl groups, each having 10 to 30 carbon atoms and a polyoxyalkylene group having a number average molecular weight of up to 5000. Such polyoxyalkylene compounds are described, for example, in EP-A 061 895 and also in U.S. Pat. No. 4,491,455. Particular polyoxyalkylene compounds are based on polyethylene glycols and polypropylene glycols having a number average molecular weight of 100 to 5000. Additionally suitable are polyoxyalkylene mono- and diesters of fatty acids having 10 to 30 carbon atoms, such as stearic acid or behenic acid.

Polar nitrogen compounds suitable as components of class (4) may be either ionic or nonionic and may have at least one substituent, or at least two substituents, in the form of a tertiary nitrogen atom of the general formula >$NR^7$ in which $R^7$ is a $C_8$- to $C_{40}$-hydrocarbon radical. The nitrogen substituents may also be quaternized i.e. be in cationic form. An example of such nitrogen compounds is that of ammonium salts and/or amides which are obtainable by the reaction of at least one amine substituted by at least one hydrocarbon radical with a carboxylic acid having 1 to 4 carboxyl groups or with a suitable derivative thereof. The amines may comprise at least one linear $C_8$- to $C_{40}$-alkyl radical. Primary amines suitable for preparing the polar nitrogen compounds mentioned are, for example, octylamine, nonylamine, decylamine, undecylamine, dodecylamine, tetradecylamine and the higher linear homologs. Secondary amines suitable for this purpose are, for example, dioctadecylamine and methylbehenylamine. Also suitable for this purpose are amine mixtures, in particular amine mixtures obtainable on the industrial scale, such as fatty amines or hydrogenated tallamines, as described, for example, in Ullmann's Encyclopedia of Industrial Chemistry, 6th Edition, "Amines, aliphatic" chapter. Acids suitable for the reaction are, for example, cyclohexane-1,2-dicarboxylic acid, cyclohexene-1,2-dicarboxylic acid, cyclopentane-1,2-dicarboxylic acid, naphthalene dicarboxylic acid, phthalic acid, isophthalic acid, terephthalic acid, and succinic acids substituted by long-chain hydrocarbon radicals.

Sulfocarboxylic acids, sulfonic acids or derivatives thereof which are suitable as cold flow improvers of class (5) are, for example, the oil-soluble carboxamides and carboxylic esters of ortho-sulfobenzoic acid, in which the sulfonic acid function is present as a sulfonate with alkyl-substituted ammonium cations, as described in EP-A 261 957.

Poly(meth)acrylic esters suitable as cold flow improvers of class (6) are either homo- or copolymers of acrylic and methacrylic esters. Preference is given to copolymers of at least two different (meth)acrylic esters which differ with regard to the esterified alcohol. The copolymer optionally comprises another different olefinically unsaturated monomer in copolymerized form. The weight-average molecular weight of the polymer is preferably 50,000 to 500,000. The polymer may be a copolymer of methacrylic acid and methacrylic esters of saturated $C_{14}$ and $C_{15}$ alcohols, the acid groups having been neutralized with hydrogenated tallamine. Suitable poly(meth)acrylic esters are described, for example, in WO 00/44857.

The cold flow improver or the mixture of different cold flow improvers is added to the middle distillate fuel or diesel fuel in a total amount of preferably 0 to 5000 ppm by weight, or 10 to 5000 ppm by weight, or 20 to 2000 ppm by weight, or 50 to 1000 ppm by weight, or 100 to 700 ppm by weight, for example of 200 to 500 ppm by weight.

Engine Oil Lubricants

In different embodiments the technology provides engine oil lubricating compositions that can be employed in internal combustion engines. The internal combustion engine may be spark ignition or compression ignition. The internal combustion engine may be a 2-stroke or 4-stroke engine. The internal combustion engine may be a passenger car engine, a light duty diesel engine, a heavy duty diesel engine, a motorcycle engine, or a 2-stroke or 4-stroke marine diesel engine. Typically the internal combustion engine may be a passenger car engine, or a heavy duty diesel internal combustion engine.

In one embodiment an engine oil lubricant composition of the invention comprises in addition to the quaternary ammonium salts of the present technology an overbased metal-containing detergent, or mixtures thereof.

Overbased detergents are known in the art. Overbased materials, otherwise referred to as overbased or superbased salts, are generally single phase, homogeneous systems characterized by a metal content in excess of that which would be present for neutralization according to the stoichiometry of the metal and the particular acidic organic compound reacted with the metal. The overbased materials are prepared by reacting an acidic material (typically an inorganic acid or lower carboxylic acid, typically carbon dioxide) with a mixture comprising an acidic organic compound, a reaction medium comprising at least one inert, organic solvent (mineral oil, naphtha, toluene, xylene, etc.) for said acidic organic material, a stoichiometric excess of a metal base, and a promoter such as a calcium chloride, acetic acid, phenol or alcohol. The acidic organic material will normally have a sufficient number of carbon atoms to provide a degree of solubility in oil. The amount of "excess" metal (stoichiometrically) is commonly expressed in terms of metal ratio. The term "metal ratio" is the ratio of the total equivalents of the metal to the equivalents of the acidic organic compound. A neutral metal salt has a metal ratio of one. A salt having 4.5 times as much metal as present in a normal salt will have metal excess of 3.5 equivalents, or a ratio of 4.5. The term "metal ratio is also explained in standard textbook entitled "Chemistry and Technology of Lubricants", Third Edition, Edited by R. M. Mortier and S. T. Orszulik, Copyright 2010, page 219, sub-heading 7.25.

The overbased metal-containing detergent may be chosen from non-sulfur-containing phenates, sulfur-containing phenates, sulfonates, salixarates, salicylates, carboxylates, and mixtures thereof, or borated equivalents thereof. The overbased detergent may be borated with a borating agent such as boric acid.

The overbased detergent may be non-sulfur containing phenates, sulfur containing phenates, sulfonates, or mixtures thereof.

An engine oil lubricant may further comprise an overbased sulfonate detergent present at 0.01 wt % to 0.9 wt %, or 0.05 wt % to 0.8 wt %, or 0.1 wt % to 0.7 wt %, or 0.2 wt % to 0.6 wt %.

The overbased sulfonate detergent may have a metal ratio of 12 to less than 20, or 12 to 18, or 20 to 30, or 22 to 25.

An engine oil lubricant composition may also include one or more detergents in addition to the overbased sulfonate.

Overbased sulfonates typically have a total base number of 250 to 600, or 300 to 500 (on an oil free basis). Overbased detergents are known in the art. In one embodiment the sulfonate detergent may be a predominantly linear alkylbenzene sulfonate detergent having a metal ratio of at least 8 as is described in paragraphs [0026] to [0037] of US Patent Application 2005065045 (and granted as U.S. Pat. No. 7,407,919). Linear alkyl benzenes may have the benzene ring attached anywhere on the linear chain, usually at the 2, 3, or 4 position, or mixtures thereof. The predominantly linear alkylbenzene sulfonate detergent may be particularly useful for assisting in improving fuel economy. In one embodiment the sulfonate detergent may be a metal salt of one or more oil-soluble alkyl toluene sulfonate compounds as disclosed in paragraphs [0046] to [0053] of US Patent Application 2008/0119378.

In one embodiment the overbased sulfonate detergent comprises an overbased calcium sulfonate. The calcium sulfonate detergent may have a metal ratio of 18 to 40 and a TBN of 300 to 500, or 325 to 425.

The other detergents may have a metal of the metal-containing detergent may also include "hybrid" detergents formed with mixed surfactant systems including phenate and/or sulfonate components, e.g., phenate/salicylates, sulfonate/phenates, sulfonate/salicylates, sulfonates/phenates/salicylates, as described; for example, in U.S. Pat. Nos. 6,429,178; 6,429,179; 6,153,565; and 6,281,179. Where, for example, a hybrid sulfonate/phenate detergent is employed, the hybrid detergent would be considered equivalent to amounts of distinct phenate and sulfonate detergents introducing like amounts of phenate and sulfonate soaps, respectively.

The other detergent may have an alkali metal, an alkaline earth metal, or zinc counter ion. In one embodiment the metal may be sodium, calcium, barium, or magnesium. Typically other detergent may be sodium, calcium, or magnesium containing detergent (typically, calcium, or magnesium containing detergent).

The other detergent may typically be an overbased detergent of sodium, calcium or magnesium salt of the phenates, sulfur-containing phenates, salixarates and salicylates. Overbased phenates and salicylates typically have a total base number of 180 to 450 TBN (on an oil free basis).

Phenate detergents are typically derived from p-hydrocarbyl phenols. Alkylphenols of this type may be coupled with sulfur and overbased, coupled with aldehyde and overbased, or carboxylated to form salicylate detergents. Suitable alkylphenols include those alkylated with oligomers of propylene, i.e. tetrapropenylphenol (i.e. p-dodecylphenol or PDDP) and pentapropenylphenol. Other suitable alkylphenols include those alkylated with alpha-olefins, isomerized alpha-olefins, and polyolefins like polyisobutylene. In one embodiment, the lubricating composition comprises less than 0.2 wt %, or less than 0.1 wt %, or even less than 0.05 wt % of a phenate detergent derived from PDDP. In one embodiment, the lubricant composition comprises a phenate detergent that is not derived from PDDP.

The overbased detergent may be present at 0 wt % to 10 wt %, or 0.1 wt % to 10 wt %, or 0.2 wt % to 8 wt %, or 0.2 wt % to 3 wt %. For example in a heavy duty diesel engine the detergent may be present at 2 wt % to 3 wt % of the lubricant composition. For a passenger car engine the detergent may be present at 0.2 wt % to 1 wt % of the lubricant composition. In one embodiment, an engine oil lubricant composition comprises at least one overbased detergent with a metal ratio of at least 3, or at least 8, or at least 15.

In an embodiment an engine oil lubricant composition comprising the imide quats of the present technology may further include a dispersant, or mixtures thereof. The dispersant may be chosen from a succinimide dispersant, a Mannich dispersant, a succinamide dispersant, a polyolefin succinic acid ester, amide, or ester-amide, or mixtures thereof.

In one embodiment an engine oil lubricant composition includes a dispersant or mixtures thereof. The dispersant may be present as a single dispersant. The dispersant may be present as a mixture of two or more (typically two or three) different dispersants, wherein at least one may be a succinimide dispersant.

The succinimide dispersant may be derived from an aliphatic polyamine, or mixtures thereof. The aliphatic polyamine may be aliphatic polyamine such as an ethylenepolyamine, a propylenepolyamine, a butylenepolyamine, or mixtures thereof. In one embodiment the aliphatic polyamine may be ethylenepolyamine. In one embodiment the aliphatic polyamine may be chosen from ethylenediamine, diethylenetriamine, triethylenetetramine, tetraethylenepentamine, pentaethylenehexamine, polyamine still bottoms, and mixtures thereof.

In one embodiment the dispersant may be a polyolefin succinic acid ester, amide, or ester-amide. For instance, a polyolefin succinic acid ester may be a polyisobutylene succinic acid ester of pentaerythritol, or mixtures thereof. A polyolefin succinic acid ester-amide may be a polyisobutylene succinic acid reacted with an alcohol (such as pentaerythritol) and an amine (such as a diamine, typically diethyleneamine).

The dispersant may be an N-substituted long chain alkenyl succinimide. An example of an N-substituted long chain alkenyl succinimide is polyisobutylene succinimide. Typically the polyisobutylene from which polyisobutylene succinic anhydride may be derived has a number average molecular weight of 350 to 5000, or 550 to 3000 or 750 to 2500. Succinimide dispersants and their preparation are disclosed, for instance in U.S. Pat. Nos. 3,172,892, 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, Re 26,433, and 6,165,235, 7,238,650 and EP Patent Application 0 355 895 A.

The dispersants may also be post-treated by conventional methods by a reaction with any of a variety of agents. Among these are boron compounds (such as boric acid), urea, thiourea, dimercaptothiadiazoles, carbon disulfide, aldehydes, and ketones, carboxylic acids such as terephthalic acid, hydrocarbon-substituted succinic anhydrides, maleic anhydride, nitriles, epoxides, and phosphorus compounds. In one embodiment the post-treated dispersant is borated. In one embodiment the post-treated dispersant may be reacted with dimercaptothiadiazoles. In one embodiment the post-treated dispersant may be reacted with phosphoric or phosphorous acid. In one embodiment the post-treated dispersant may be reacted with terephthalic acid and boric acid (as described in US Patent Application US2009/0054278.

In one embodiment the dispersant may be borated or non-borated. Typically a borated dispersant may be a succinimide dispersant. In one embodiment, the ashless dispersant may be boron-containing, i.e., has incorporated boron and delivers said boron to the lubricant composition. The boron-containing dispersant may be present in an amount to deliver at least 25 ppm boron, at least 50 ppm boron, or at least 100 ppm boron to the lubricant composition. In one embodiment, the lubricant composition may be free of a boron-containing dispersant, i.e. delivers no more than 10 ppm boron to the final formulation.

The dispersant may be prepared/obtained/obtainable from reaction of succinic anhydride by an "ene" or "thermal" reaction, by what may be referred to as a "direct alkylation process." The "ene" reaction mechanism and general reaction conditions are summarized in "Maleic Anhydride", pages, 147-149, Edited by B. C. Trivedi and B. C. Culbertson and Published by Plenum Press in 1982. The dispersant prepared by a process that includes an "ene" reaction may be a polyisobutylene succinimide having a carbocyclic ring present on less than 50 mole %, or 0 to less than 30 mole %, or 0 to less than 20 mole %, or 0 mole % of the dispersant molecules. The "ene" reaction may have a reaction temperature of 180° C. to less than 300° C., or 200° C. to 250° C., or 200° C. to 220° C.

The dispersant may also be obtained/obtainable from a chlorine-assisted process, often involving Diels-Alder chemistry, leading to formation of carbocyclic linkages. The process is known to a person skilled in the art. The chlorine-assisted process may produce a dispersant that is a polyisobutylene succinimide having a carbocyclic ring present on 50 mole % or more, or 60 to 100 mole % of the dispersant molecules. Both the thermal and chlorine-assisted processes are described in greater detail in U.S. Pat. No. 7,615,521, columns 4-5 and preparative examples A and B.

The dispersant may have a carbonyl to nitrogen ratio (CO:N ratio) of 5:1 to 1:10, 2:1 to 1:10, or 2:1 to 1:5, or 2:1 to 1:2. In one embodiment the dispersant may have a CO:N ratio of 2:1 to 1:10, or 2:1 to 1:5, or 2:1 to 1:2, or 1:1.4 to 1:0.6.

In one embodiment the dispersant may be a succinimide dispersant may comprise a polyisobutylene succinimide, wherein the polyisobutylene from which polyisobutylene succinimide is derived has a number average molecular weight of 350 to 5000, or 750 to 2500. The dispersant may be present at 0 wt % to 20 wt %. 0.1 wt % to 15 wt %, or 0.5 wt % to 9 wt %, or 1 wt % to 8.5 wt % or 1.5 to 5 wt % of the lubricant composition.

In one embodiment an engine oil lubricant composition comprising the imide quats of the present technology may be a lubricant composition further comprising a molybdenum compound. The molybdenum compound may be an antiwear agent or an antioxidant. The molybdenum compound may be chosen from molybdenum dialkyldithiophosphates, molybdenum dithiocarbamates, amine salts of molybdenum compounds, and mixtures thereof. The molybdenum compound may provide the lubricant composition with 0 to 1000 ppm, or 5 to 1000 ppm, or 10 to 750 ppm 5 ppm to 300 ppm, or 20 ppm to 250 ppm of molybdenum.

In another embodiment an engine oil lubricant composition comprising the imide quats of the present technology may further comprise an antioxidant. Antioxidants include sulfurized olefins, diarylamines, alkylated diarylamines, hindered phenols, molybdenum compounds (such as molybdenum dithiocarbamates), hydroxyl thioethers, or mixtures thereof. In one embodiment the lubricant composition includes an antioxidant, or mixtures thereof. The antioxidant may be present at 0 wt % to 15 wt %, or 0.1 wt % to 10 wt %, or 0.5 wt % to 5 wt %, or 0.5 wt % to 3 wt %, or 0.3 wt % to 1.5 wt % of the lubricant composition.

In one embodiment an engine oil lubricant composition comprising the imide quats of the present technology and further comprises a phenolic or an aminic antioxidant or mixtures thereof, and wherein the antioxidant is present at 0.1 wt % to 3 wt %, or 0.5 wt % to 2.75 wt %, or 1 wt % to 2.5 wt %.

The diarylamine or alkylated diarylamine may be a phenyl-α-naphthylamine (PANA), an alkylated diphenylamine, or an alkylated phenylnapthylamine, or mixtures thereof. The alkylated diphenylamine may include di-nonylated diphenylamine, nonyl diphenylamine, octyl diphenylamine, di-octylated diphenylamine, di-decylated diphenylamine, decyl diphenylamine and mixtures thereof. In one embodiment the diphenylamine may include nonyl diphenylamine, dinonyl diphenylamine, octyl diphenylamine, dioctyl diphenylamine, or mixtures thereof. In one embodiment the alkylated diphenylamine may include nonyl diphenylamine, or dinonyl diphenylamine. The alkylated diarylamine may include octyl, di-octyl, nonyl, di-nonyl, decyl or di-decyl phenylnapthylamines.

The hindered phenol antioxidant often contains a secondary butyl and/or a tertiary butyl group as a sterically hindering group. The phenol group may be further substituted with a hydrocarbyl group (typically linear or branched alkyl) and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In one embodiment the hindered phenol antioxidant may be an ester and may include, e.g., Irganox™ L-135 from Ciba. A more detailed description of suitable ester-containing hindered phenol antioxidant chemistry is found in U.S. Pat. No. 6,559,105.

Examples of molybdenum dithiocarbamates, which may be used as an antioxidant, include commercial materials sold under the trade names such as Molyvan 822®, Molyvan® A and Molyvan® 855 from R. T. Vanderbilt Co., Ltd., and Adeka Sakura-Lube™ S-100, S-165, S-600 and 525, or mixtures thereof.

In one embodiment an engine oil lubricant composition comprising the imide quats of the present technology further includes a viscosity modifier. The viscosity modifier is known in the art and may include hydrogenated styrene-butadiene rubbers, ethylene-propylene copolymers, ethylene copolymers with propylene and higher olefins, polymethacrylates, polyacrylates, hydrogenated styrene-isoprene polymers, hydrogenated diene polymers, polyalkyl styrenes, polyolefins, esters of maleic anhydride-olefin copolymers (such as those described in International Application WO 2010/014655), esters of maleic anhydride-styrene copolymers, or mixtures thereof. The viscosity modifier may include a block copolymer comprising (i) a vinyl aromatic monomer block and (ii), a conjugated diene olefin monomer block (such as a hydrogenated styrene-butadiene copolymer or a hydrogenated styrene-isoprene copolymer), a polymethacrylate, an ethylene-alpha olefin copolymer, a hydrogenated star polymer comprising conjugated diene monomers such as butadiene or isoprene, or a star polymer of polymethacrylate, or mixtures thereof.

In an embodiment the viscosity modifier may be a dispersant viscosity modifier. The dispersant viscosity modifier may include functionalized polyolefins, for example, ethylene-propylene copolymers that have been functionalized with an acylating agent such as maleic anhydride and an amine.

In one particular embodiment the dispersant viscosity modifier comprises an olefin copolymer further functionalized with a dispersant amine group. Typically, the olefin copolymer is an ethylene-propylene copolymer. The olefin copolymer has a number average molecular weight of 5000 to 20,000, or 6000 to 18,000, or 7000 to 15,000. The olefin copolymer may have a shear stability index of 0 to 20, or 0 to 10, or 0 to 5 as measured by the Orbahn shear test (ASTM D6278) as described above.

The formation of a dispersant viscosity modifier is well known in the art. The dispersant viscosity modifier may include for instance those described in U.S. Pat. No. 7,790,661 column 2, line 48 to column 10, line 38.

In one embodiment the dispersant viscosity modifier may be prepared by grafting of an olefinic carboxylic acid acylating agent onto a polymer of 15 to 80 mole percent of ethylene, from 20 to 85 mole percent of $C_{3-10}$ α-monoolefin, and from 0 to 15 mole percent of non-conjugated diene or triene, said polymer having an average molecular weight ranging from 5000 to 20,000, and further reacting said grafted polymer with an amine (typically an aromatic amine).

The dispersant viscosity modifier may include functionalized polyolefins, for example, ethylene-propylene copolymers that have been functionalized with an acylating agent such as maleic anhydride and an amine; polymethacrylates functionalized with an amine, or styrene-maleic anhydride copolymers reacted with an amine. Suitable amines may be aliphatic or aromatic amines and polyamines. Examples of suitable aromatic amines include nitroaniline, aminodiphenylamine (ADPA), hydrocarbylene coupled polyaromatic amines, and mixtures thereof. More detailed description of dispersant viscosity modifiers are disclosed in International Publication WO2006/015130 or U.S. Pat. Nos. 4,863,623; 6,107,257; 6,107,258; 6,117,825; and 7,790,661.

In one embodiment the dispersant viscosity modifier may include those described in U.S. Pat. No. 4,863,623 (see column 2, line 15 to column 3, line 52) or in International Publication WO2006/015130 (see page 2, paragraph [0008] and preparative examples are described paragraphs [0065] to [0073]). In one embodiment the dispersant viscosity modifier may include those described in U.S. Pat. No. 7,790,661 column 2, line 48 to column 10, line 38.

In one embodiment an engine oil lubricant composition comprising the imide quat disclosed herein further comprises a dispersant viscosity modifier. The dispersant viscosity modifier may be present at 0 wt % to 5 wt %, or 0 wt % to 4 wt %, or 0.05 wt % to 2 wt %, or 0.2 wt % to 1.2 wt % of the lubricant composition.

In one embodiment an engine oil lubricant composition comprising the imide quats of the present technology further includes a friction modifier. In one embodiment the friction modifier may be chosen from long chain fatty acid derivatives of amines, long chain fatty esters, or derivatives of long chain fatty epoxides; fatty imidazolines; amine salts of alkylphosphoric acids; fatty alkyl tartrates; fatty alkyl tartrimides; fatty alkyl tartramides; fatty malic esters and imides, fatty (poly)glycolates; and fatty glycolamides. The friction modifier may be present at 0 wt % to 6 wt %, or 0.01 wt % to 4 wt %, or 0.05 wt % to 2 wt %, or 0.1 wt % to 2 wt % of the lubricant composition. As used herein the term "fatty alkyl" or "fatty" in relation to friction modifiers means a carbon chain having 10 to 22 carbon atoms, typically a straight carbon chain.

Examples of suitable friction modifiers include long chain fatty acid derivatives of amines, fatty esters, or fatty epoxides; fatty imidazolines such as condensation products of carboxylic acids and polyalkylene-polyamines; amine salts of alkylphosphoric acids; fatty alkyl tartrates; fatty alkyl tartrimides; fatty alkyl tartramides; fatty phosphonates; fatty phosphites; borated phospholipids, borated fatty epoxides; glycerol esters such as glycerol mono-oleate; borated glycerol esters; fatty amines; alkoxylated fatty amines; borated alkoxylated fatty amines; hydroxyl and polyhydroxy fatty amines including tertiary hydroxy fatty amines; hydroxy alkyl amides; metal salts of fatty acids; metal salts of alkyl salicylates; fatty oxazolines; fatty ethoxylated alcohols; condensation products of carboxylic acids and polyalkylene polyamines; or reaction products from fatty carboxylic acids with guanidine, aminoguanidine, urea, or thiourea and salts thereof.

Friction modifiers may also encompass materials such as sulfurized fatty compounds and olefins, molybdenum dialkyldithiophosphates, molybdenum dithiocarbamates, sunflower oil or soybean oil monoester of a polyol and an aliphatic carboxylic acid.

In one embodiment the friction modifier may be a long chain fatty acid ester. In another embodiment the long chain fatty acid ester may be a mono-ester and in another embodiment the long chain fatty acid ester may be a triglyceride.

An engine oil lubricant composition comprising the imide quats of the present technology optionally further includes at least one antiwear agent. Examples of suitable antiwear agents include titanium compounds, tartaric acid derivatives such as tartrate esters, amides or tartrimides, malic acid derivatives, citric acid derivatives, glycolic acid derivatives, oil soluble amine salts of phosphorus compounds different from that of the invention, sulfurized olefins, metal dihydrocarbyldithiophosphates (such as zinc dialkyldithiophosphates), phosphites (such as dibutyl phosphite), phosphonates, thiocarbamate-containing compounds, such as thiocarbamate esters, thiocarbamate amides, thiocarbamic ethers, alkylene-coupled thiocarbamates, and bis(S-alkyldithiocarbamyl)disulfides.

The antiwear agent may in one embodiment include a tartrate or tartrimide as disclosed in International Publication WO 2006/044411 or Canadian Patent CA 1 183 125. The tartrate or tartrimide may contain alkyl-ester groups, where the sum of carbon atoms on the alkyl groups is at least 8. The antiwear agent may in one embodiment include a citrate as is disclosed in US Patent Application 20050198894.

Another class of additives includes oil-soluble titanium compounds as disclosed in U.S. Pat. No. 7,727,943 and US2006/0014651. The oil-soluble titanium compounds may function as antiwear agents, friction modifiers, antioxidants, deposit control additives, or more than one of these functions. In one embodiment the oil soluble titanium compound is a titanium (IV) alkoxide. The titanium alkoxide is formed from a monohydric alcohol, a polyol or mixtures thereof. The monohydric alkoxides may have 2 to 16, or 3 to 10 carbon atoms. In one embodiment, the titanium alkoxide is titanium (IV) isopropoxide. In one embodiment, the titanium alkoxide is titanium (IV) 2-ethylhexoxide. In one embodiment, the titanium compound comprises the alkoxide of a vicinal 1,2-diol or polyol. In one embodiment, the 1,2-vicinal diol comprises a fatty acid mono-ester of glycerol, often the fatty acid is oleic acid.

In one embodiment, the oil soluble titanium compound is a titanium carboxylate. In one embodiment the titanium (IV) carboxylate is titanium neodecanoate.

An engine oil lubricant composition comprising the imide quats of the present technology may further include a phosphorus-containing antiwear agent different from that of the invention. Typically the phosphorus-containing antiwear agent may be a zinc dialkyldithiophosphate, phosphite, phosphate, phosphonate, and ammonium phosphate salts, or mixtures thereof.

In one embodiment an engine oil lubricant composition may further comprise a phosphorus-containing antiwear agent, typically zinc dialkyldithiophosphate. Zinc dialkyldithiophosphates are known in the art. Examples of zinc dithiophosphates include zinc isopropyl methylamyl dithiophosphate, zinc isopropyl isooctyl dithiophosphate, zinc di(cyclohexyl) dithiophosphate, zinc isobutyl 2-ethylhexyl dithiophosphate, zinc isopropyl 2-ethylhexyl dithiophosphate, zinc isobutyl isoamyl dithiophosphate, zinc isopropyl n-butyl dithiophosphate, and combinations thereof. Zinc dialkyldithiophosphate may be present in amount to provide 0.01 wt % to 0.1 wt % phosphorus to the lubricating composition, or to provide 0.015 wt % to 0.075 wt % phosphorus, or 0.02 wt % to 0.05 wt % phosphorus to the lubricating composition.

In one embodiment, an engine oil lubricant composition further comprises one or more zinc dialkyldithiophosphate such that the amine (thio)phosphate additive of the invention provides at least 50% of the total phosphorus present in the lubricating composition, or at least 70% of the total phosphorus, or at least 90% of the total phosphorus in the lubricating composition. In one embodiment, the lubricant composition is free or substantially free of a zinc dialkyldithiophosphate. The antiwear agent may be present at 0 wt % to 3 wt %, or 0.1 wt % to 1.5 wt %, or 0.5 wt % to 0.9 wt % of the lubricant composition.

In one embodiment an engine oil lubricant composition comprising the imide quats of the present technology further comprises 0.01 to 5 wt % or 0.1 to 2 wt % of an ashless antiwear agent represented by Formula:

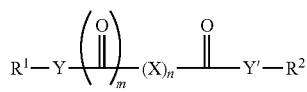

wherein

Y and Y' are independently —O—, >NH, >NR$^3$, or an imide group formed by taking together both Y and Y' groups and forming a R$^1$—N<group between two >C=O groups;

X is independently —Z—O—Z'—, >CH$_2$, >CHR$^4$, >CR$^4$R$^5$, >C(OH)(CO$_2$R$^2$), >C(CO$_2$R$^2$)$_2$, or >CHOR$^6$;

Z and Z' are independently >CH$_2$, >CHR$_4$, >CR$_4$R$^5$, >C(OH)(CO$_2$R$^2$), or >CHOR$_6$;

n is 0 to 10, with the proviso that when n=1, X is not >CH$_2$, and when n=2, both X's are not >CH$_2$;

m is 0 or 1;

R$^1$ is independently hydrogen or a hydrocarbyl group, typically containing 1 to 150 carbon atoms, with the proviso that when R$^1$ is hydrogen, m is 0, and n is more than or equal to 1;

R$^2$ is a hydrocarbyl group, typically containing 1 to 150 carbon atoms;

R$^3$, R$^4$ and R$^5$ are independently hydrocarbyl groups; and

R$^6$ is hydrogen or a hydrocarbyl group, typically containing 1 to 150 carbon atoms.

In one embodiment an engine oil lubricant composition comprising the imide quats of the present technology further comprises 0.01 to 5 wt % or 0.1 to 2 wt % of an ashless antiwear agent that may be a compound obtained/obtainable by a process comprising reacting a glycolic acid, a 2-halo-acetic acid, or a lactic acid, or an alkali or alkaline metal salt thereof, (typically glycolic acid or a 2-halo-acetic acid) with at least one member selected from the group consisting of an amine, an alcohol, and an amino alcohol. For example the compound may be represented by formulae:

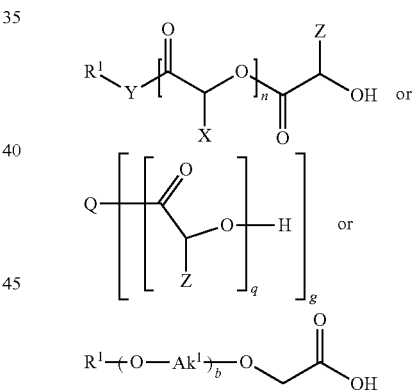

wherein

Y is independently oxygen or >NH or >NR$^1$;

R$^1$ is independently a hydrocarbyl group, typically containing 4 to 30, or 6 to 20, or 8 to 18 carbon atoms;

Z is hydrogen or methyl;

Q is the residue of a diol, triol or higher polyol, a diamine, triamine, or higher polyamine, or an aminoalcohol (typically Q is a diol, diamine or aminoalcohol)

g is 2 to 6, or 2 to 3, or 2;

q is 1 to 4, or 1 to 3 or 1 to 2;

n is 0 to 10, 0 to 6, 0 to 5, 1 to 4, or 1 to 3; and

Aki is an alkylene group containing 1 to 5, or 2 to 4 or 2 to 3 (typically ethylene) carbon atoms; and b is 1 to 10, or 2 to 8, or 4 to 6, or 4.

The compound is known and is described in International publication WO 2011/022317, and also in granted U.S. Pat. Nos. 8,404,625, 8,530,395, and 8,557,755.

INDUSTRIAL APPLICATION

In one embodiment, the invention is useful in a liquid fuel or an oil of lubricating viscosity in an internal combustion engine. The internal combustion engine may be a gasoline or diesel engine. Exemplary internal combustion engines include, but are not limited to, spark ignition and compression ignition engines; 2-stroke or 4-stroke cycles; liquid fuel supplied via direct injection, indirect injection, port injection and carburetor; common rail and unit injector systems; light (e.g. passenger car) and heavy duty (e.g. commercial truck) engines; and engines fueled with hydrocarbon and non-hydrocarbon fuels and mixtures thereof. The engines may be part of integrated emissions systems incorporating such elements as; EGR systems; aftertreatment including three-way catalyst, oxidation catalyst, $NO_x$ absorbers and catalysts, catalyzed and non-catalyzed particulate traps optionally employing fuel-borne catalyst; variable valve timing; and injection timing and rate shaping.

In one embodiment, the technology may be used with diesel engines having direct fuel injection systems wherein the fuel is injected directly into the engine's combustion chamber. The ignition pressures may be greater than 1000 bar and, in one embodiment, the ignition pressure may be greater than 1350 bar. Accordingly, in another embodiment, the direct fuel injection system maybe a high-pressure direct fuel injection system having ignition pressures greater than 1350 bar. Exemplary types of high-pressure direct fuel injection systems include, but are not limited to, unit direct injection (or "pump and nozzle") systems, and common rail systems. In unit direct injection systems the high-pressure fuel pump, fuel metering system and fuel injector are combined into one apparatus. Common rail systems have a series of injectors connected to the same pressure accumulator, or rail. The rail in turn, is connected to a high-pressure fuel pump. In yet another embodiment, the unit direct injection or common rail systems may further comprise an optional turbocharged or supercharged direct injection system.

In a further embodiment, the imide quat technology is useful for providing at least equivalent, if not improved detergency (deposit reduction and/or prevention) performance in both the traditional and modern diesel engine compared to a 1000 $M_n$ quaternary ammonium compound. In yet another embodiment, the disclosed technology may be used to improve the cold temperature operability or performance of a diesel fuel (as measured by the ARAL test).

In yet another embodiment, a lubricating composition comprising an imide quat is useful for lubricating an internal combustion engine (for crankcase lubrication).

Embodiments of the present technology may provide at least one of antiwear performance, friction modification (particularly for enhancing fuel economy), detergent performance (particularly deposit control or varnish control), dispersancy (particularly soot control, sludge control, or corrosion control).

Deposit Control

As fuel burns inside an engine, solid carbonaceous by-products may be produced. The solid by-products may stick to the interior walls of the engine and are often referred to as deposits. If left unchecked, engines fouled by deposits may experience a loss in engine power, fuel efficiency, or drivability.

In traditional diesel engines operating at low pressures (i.e., <35 MPa), deposits form on the fuel injector tips and in the spray holes. These injector tip deposits can disrupt the spray pattern of the fuel, potentially causing a reduction in power and fuel economy. Deposits may also form inside the injectors in addition to forming on the tips. These internal deposits are commonly called internal diesel injector deposits (IDIDs). It is believed that IDIDs have a minor impact, if any on the operation of traditional diesel engines operating at low pressures.

With the introduction of diesel engines equipped with high pressure common rail fuel injector systems (i.e., >35 MPa), however, IDIDs may be more problematic than in traditional diesel engines. In high pressure common rail fuel injector systems, IDIDs can form on injector moving parts, such as the needle and command piston or control valve. IDIDs can hinder the movement of the injector parts, impairing the injection timing and the quantity of fuel injected. Since modern diesel engines operate on precise multiple injection strategies in order to maximize efficiency and performance of combustion, IDIDs can have a serious adverse effect on engine operation and vehicle drivability.

High pressure common rail fuel injector systems are both more susceptible and more prone to IDID formation. These advanced systems have tighter tolerances due to their extremely high operating pressures. Likewise, in some cases the clearance between moving parts in the injectors is only a few microns or less. As such, advanced diesel fuel systems are more susceptible to IDIDs. Deposits may be likely to form in these systems because of their higher operating temperatures which can oxidize and decompose the chemically unstable components of the diesel fuel. Another factor that may also contribute to IDID issues in high pressure common rail systems is that these injectors often have lower activation forces making them even more prone to sticking than in high pressure systems. The lower activation forces may also cause some of the fuel to "leak back" into the injectors, which may also contribute to IDID.

Without limiting this specification to one theory of operation, it is believed that IDIDs are formed from when the hydrophilic-lipophilic balance (HLB) of sparingly soluble contaminants moves to a level where the hydrophilic head group dominates over the lipophilic tail. As the length of the lipophilic tail decreases, the hydrophilic head group begins to dominate. The structure of the tail (branched versus linear) and/or may also affect the solubility of the contaminants. In addition, as the polarity of the head group sparingly soluble contaminants increase, its solubility decreases. While there may be multiple causes and sources of IDID, two types of IDIDs have been identified; 1) metal (sodium) carboxylate-type IDIDs, often referred to as "metal soaps" or "sodium soaps", and 2) amide-type IDIDs, often referred to as "amide lacquers".

Advanced chemical analysis techniques have been used to obtain more detailed structural information on IDIDs to help identify the sources of the problem. Detailed analysis of metal soap-type IDIDs has helped identify corrosion inhibitors, such as alkenyl succinic acids, as culprits in IDID formation. The corrosion inhibitors, for example, dodecenyl succinic acid (DDSA) and hexadecenyl succinic acid (HDSA) (two commonly used pipeline corrosion inhibitors in the petroleum industry), pick up trace levels of sodium and other metals in the fuel left over from the refinery process. Tests have been conducted using engines compliant with US Tier 3 emission standards to explore the underlying structure activity relationships of sodium soap formation. Without limiting this specification to one theory of operation, it is believed that the formation of metal soap IDIDs is dependent upon the size (number of carbons) of the hydrocarbon tail of the "soap" and the number of carboxylic acids groups ($CO_2H$) in the head group of the corrosion inhibitor. It was observed that the tendency to form deposits increases when the inhibitor had a short tail and multiple carboxylic acids in the head group. In other words, dicarboxylic acid corrosion inhibitors with a lower number average molecular weight (MW) ranging between 280 and 340, have a greater tendency to form sodium soap deposits than corrosion inhibitors with a higher number average molecular weight. Persons of ordinary skill in the art will understand that there may be some low molecular weight polymers present in corrosion inhibitors with a number average molecular weight above 340.

These laboratory tests have also shown that deposits can form with as little as 0.5 to 1 ppm of sodium in the fuel along with 8 to 12 ppm of a corrosion inhibitor, such as DDSA or HDSA, and it is possible that real world concentrations may be lower with deposits occurring over longer periods of time, such as 0.01 to 0.5 ppm metal with 1 to 8 ppm corrosion inhibitor.

These metal soaps can be referred to as low molecular weight soaps, and can be represented, for example, by structures of:

wherein R* is a linear, branched or cyclic hydrocarbyl group having 10 to 36 carbon atoms, or 12 to 18, or 12 to 16 carbon atoms, M⁺ is a metal contaminant, such as sodium, calcium, or potassium, and x is an integer from 1 to 4, 2 to 3, or 2. One class of low molecular weight soaps are those represented by formula:

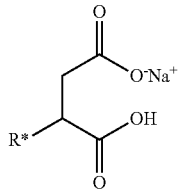

wherein R* is defined as above. Particular soaps include DDSA or HDSA soaps. These low molecular weight soaps may have a number average molecular weight ($M_n$) ranging between 280 and 340.

Amide lacquer formation is less certain but it has been suggested that it is derived from polyisobutylene succinimides (PIBSIs) with low number average molecular weight ($M_n$) which are added to diesel fuel to control nozzle fouling. Low molecular weight PIBSIs may have an average $M_n$ of 400 or less using gel permeation chromatography (GPC) and a polystyrene calibration curve. Alternatively, low $M_n$ PIBSIs may have an average $M_n$ of 200 to 300. These low molecular weight PIBSIs may be byproducts formed from low molecular weight PIBS present in the production process. While generally higher molecular weight polyisobutylene (PIB) with an average $M_n$ of 1000 is used to generate the PIBSIs, low molecular weight PIBs may be present as contaminants. Low molecular weight PIBSIs may also form when increasing the reaction temperature to remove excess reactants or catalysts. Again, while completely eliminating low $M_n$ PIBSIs from anti-foulants might result in reducing IDID formation, complete elimination might not be practical. Accordingly, low $M_n$ PIBSIs may be present in an amount of 5 wt % or less of a total weight of the PIBIs used. It is hypothesized, without limiting this specification to one theory of operation, that the low molecular weight portion of the PIBSI is responsible for deposit formation as it is only sparingly soluble in diesel and thus deposits on the injector surface. In fact, amide lacquer IDIDs have been shown to be linked to low molecular weight species by demonstrating that amide lacquer IDIDs can be produced in US Tier 3-compliant engines using a low molecular weight PIBSI fraction. Here again, laboratory tests have shown that as little as 5 ppm of the low molecular weight PIBSI can cause deposit issues and it is possible that real world concentrations may be lower with deposits occurring over longer periods of time, such as from 0.01 to 5 ppm low molecular weight PIBSI.

Such low molecular weight PIBSI fractions can be represented, for example, by structure:

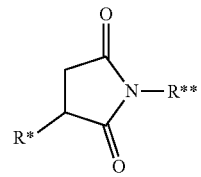

wherein R* is as defined above, and R** is a hydrocarbyl polyamine such as an ethylene polyamine.

The degree of bismaleation of the low molecular weight PIBSI may also affect the polarity of the head group, thereby reducing the PIBSI's solubility in the fuel.

Another factor that may contribute to IDID formation is the change in diesel fuel to sulfur-free diesel fuel. Sulfur-free diesel fuel is produced by hydrotreating wherein polyaromatics are reduced, thereby lowering the boiling point of the final fuel. As the final fuel is less aromatic, it is also less polar and therefore less able to solubilize sparingly soluble contaminants such as metal soaps or amide lacquers.

Surprisingly, the formation of IDIDs can be reduced in a fuel containing low molecular weight soaps or low molecular weight PIBSI fractions by adding to the fuel the imide quats with a number average molecular weight ranging from 300 to 750 described herein. Thus, an embodiment of the present technology includes fuel compositions comprising at least one low molecular weight soap and the imide quat as described above.

In another embodiment, a method of reducing and/or preventing internal diesel injector deposits is disclosed. The method may comprise employing a fuel composition comprising the imide quat as described above. The fuel may have a low molecular weight soap present therein. In an embodiment, the low molecular weight soap can be derived from the presence of from 0.01 to 5 ppm of a metal and 1 to 12, or 1 to 8, or 8 to 12 ppm of a corrosion inhibitor. Exemplary metals include, but are not limited to, sodium, calcium, and potassium. The corrosion inhibitors may comprise an alkenyl succinic acid such as dodecenyl succinic acid (DDSA) or hexadecenyl succinic acid (HDSA). In yet another embodiment of the present technology the fuel composition may have a low molecular weight polyisobutylene succinimides (PIBSI) present therein. The low molecular weight PIBSI may be present in the fuel at greater than 0.01 ppm, such as, for example, 5 to 25 ppm, or from 0.01 to 5 ppm of a low molecular weight PIBSI.

In a further embodiment, the technology may include a method of cleaning-up deposits in a diesel engine, such as, a diesel engine having a high pressure (i.e., above 35 MPa) common rail injector system, by operating the engine with a fuel containing an imide quat therein. In an embodiment, the clean-up method includes reducing and/or preventing IDID causing deposits derived from the presence of a low molecular weight soap. In an embodiment, the clean-up method includes reducing and/or preventing IDID causing deposits derived from the presence of a low molecular weight PIBSI.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include: hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring); substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulfoxy); hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

It is known that some of the materials described above may interact in the final formulation, so that the components of the final formulation may be different from those that are initially added. For instance, metal ions (of, e.g., a detergent) can migrate to other acidic or anionic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

EXAMPLES

The invention will be further illustrated by the following examples, which sets forth particularly advantageous embodiments. While the examples are provided to illustrate the present invention, they are not intended to limit it.

Example 1—Formation of Quaternizable Compound—Hexadecenyl Succinic Anhydride (HDSA) and Dimethylaminopropylamine (DMAPA)

HDSA (700 g, 2.24 moles) is charged to a 2-liter flask equipped with a water condenser and Dean Stark trap, a thermocouple, a dropping funnel, an overhead stirrer and Nitrogen inlet and heated to 90° C.

DMAPA (220.5 g, 2.24 moles) is added to the flask via the dropping funnel over 90 minutes. The batch temperature is kept below 120° C. while adding the DMAPA.

Once all the DMAPA is added, the reaction is slowly heated to 150° C. and maintained at that temperature for 3 hours. Approximately 33 g of water is collected in the Dean Stark apparatus while heating. The remaining product is an HDSA/DMAPA quaternizable compound.

Example 2—Formation of a HDSA/DMAPA Quaternary Ammonium Salt using Dimethyl Sulfate (an imide/dimethyl sulfate quat)

The HDSA/DMAPA (390 g, 0.98 moles) (product of Example 1) is charged to a 2 liter flask equipped with a water condenser, a thermocouple, a dropping funnel, an overhead stirrer and a nitrogen inlet.

Diluent oil (502 g), such as mineral oil of type SN 100-SN 150, is added to the flask and the flask is heated to 60° C. under agitation and nitrogen atmosphere.

Dimethyl sulfate (112.4 g, 0.89 moles) is then added drop wise to the flask. An exotherm of 29° C. is noted taking the batch temperature from 59.6° C. to 88.4° C. The batch is then maintained at 90° C. for two hours before cooling back to 50° C. and decanting the imide/dimethyl sulfate quat into storage vessel.

Example 3—Formation of an HDSA/DMAPA Quaternary Ammonium Salt Using Propylene Oxide (an Imide/Propylene Oxide Quat)

The HDSA/DMAPA quaternizable compound (420 g, 1.01 moles) (product of Example 1) is added to a 1-liter flask equipped with a water condenser, a thermocouple, a septum-needle syringe pump set-up, an overhead stirrer and a nitrogen inlet.

2-ethylhexanol (189.6 g, 1.46 moles), acetic acid (60.7 g, 1.01 moles) ? is also charged to the 1-liter flask. The batch is then heated to 75° C., under agitation and nitrogen atmosphere. Propylene oxide (88.1 g, 1.51 moles) is added via a syringe pump over 2 hours. The batch is then held for 3 hours at 75° C. before being cooled back to 50° C. The imide/propylene oxide quat is then decanted into a storage vessel.

Example 4—Formation of an HDSA/DMAPA Quaternary Ammonium Salt Using Propylene Oxide and Water (an Imide/Propylene Oxide Quat)

A 1-liter flask is equipped with a water condenser, a thermocouple, a syringe pump, an overhead stirrer and nitrogen inlet. The HDSA/DMAPA quaternizable compound (420 g, 1.01 moles) (product of Example 1) is added to the flask along with 2-ethylhexanol (189.6 g, 1.46 moles), water (10.5 g, 0.6 moles) and acetic acid (60.7 g, 1.01 moles).

The batch is then heated to 75° C., under agitation and nitrogen atmosphere and the propylene oxide (145 g, 2.50 moles) added via syringe pump over 2 hours. The batch is then held for 3 hours at 75° C. before being cooled back to 50° C. and decanted into a storage vessel.

Example 5—Formation of Quaternizable Compound—Dodecenyl Succinic Anhydride (DDSA) and Dimethylaminopropylamine (DMAPA)

DDSA (700 g, 2.66 moles) is charged to a 2-liter flask equipped with a water condenser and Dean Stark trap, a thermocouple, a dropping funnel, an overhead stirrer and nitrogen inlet and heated to 90° C.

DMAPA (272.16 g, 2.66 moles) is added to the flask via the dropping funnel over 90 minutes. The batch temperature is kept below 120° C. while adding the DMAPA.

Once all the DMAPA is added, the reaction is slowly heated to 150° C. and maintained at that temperature for 3 hours. Approximately 70 g of water is collected in the Dean Stark apparatus while heating. The remaining product is the 270 $M_n$ DDSA/DMAPA quaternizable compound.

Example 6—Formation of a DDSA/DMAPA Quaternary Ammonium Salt Using Dimethyl Sulfate (an Imide/Dimethyl Sulfate Quat)

The DDSA/DMAPA (390 g, 1.12 moles) (product of Example 5) is charged to a 2 liter flask equipped with a water condenser, a thermocouple, a dropping funnel, an overhead stirrer and a nitrogen inlet.

Diluent oil (516 g), such as mineral oil of type SN 100-SN 150, is added to the flask and the flask is heated to 60° C. under agitation and nitrogen atmosphere.

Dimethyl sulfate (126 g, 1.00 moles) is then added drop wise to the flask. An exotherm of about 30° C. is noted taking the batch temperature from 60° C. to 90° C. The batch is then maintained at 90° C. for two hours before cooling back to 50° C. and decanting the imide/dimethyl sulfate quat into storage vessel.

Example 7—Formation of a DDSA/DMAPA Quaternary Ammonium Salt Using Propylene Oxide (an Imide/Propylene Oxide Quat)

The DDSA/DMAPA quaternizable compound (420 g, 1.26 moles) (product of Example 6) is added to a 1-liter flask equipped with a water condenser, a thermocouple, a septum-needle syringe pump set-up, an overhead stirrer and a nitrogen inlet.

2-ethylhexanol (202 g, 1.55 moles) and acetic acid (76 g, 1.26 moles) is also charged to the 1-liter flask.

The batch is then heated to 75° C., under agitation and nitrogen atmosphere. Propylene oxide (110.2 g, 1.89 moles) is added via a syringe pump over 2 hours. The batch is then held for 3 hours at 75° C. before being cooled back to 50° C. The imide/propylene oxide quat is then decanted into a storage vessel.

Example 8—Formation of a DDSA/DMAPA Quaternary Ammonium Salt Using Propylene Oxide and Water (an Imide/Propylene Oxide Quat)

A 1 liter-flask is equipped with a water condenser, a thermocouple, a syringe pump, an overhead stirrer and nitrogen inlet.

The DDSA/DMAPA quaternizable compound (420 g, 1.26 moles) (product of Example 6) is added to the flask along with 2-ethylhexanol (202 g, 1.55 moles), water (13.6 g, 0.75 moles) and acetic acid (76 g, 1.26 moles).

The batch was then heated to 75° C., under agitation and nitrogen atmosphere and the propylene oxide (182.7 g, 3.15 moles) added via syringe pump over 2 hours. The batch was then held for 3 hours at 75° C. before being cooled back to 50° C. and decanted into a storage vessel.

Additional examples of making the imide quats are shown in Table 2.

TABLE 2

| Example | Protic Solvent (wt %*) | Quaternizing Agent (mole ratio***) | Water (wt %*) | Acid (mole ratio**) | Quaternizable Compound (mole ratio) | Temp (° C.) | Total Quat Produced (wt %) | |
|---|---|---|---|---|---|---|---|---|
| | | | | | | | ESIMS | NMR |
| A | 15 | 3 | 2 | 1 | balance | 60 | 89 | 90 |
| B | 15 | 2.5 | 2.5 | 1 | balance | 70 | 89 | 97 |
| C | 15 | 2.5 | 2.25 | 1 | balance | 60 | 90 | 95 |
| D | 15 | 3 | 2.5 | 1 | balance | 65 | 90 | 95 |
| E | 15 | 2.75 | 2 | 1 | balance | 70 | 86 | 94 |
| F | 15 | 3 | 2.25 | 1 | balance | 70 | 88 | 95 |
| G | 15 | 2.5 | 2 | 1 | balance | 65 | 85 | 91 |
| H | 15 | 2.75 | 2.25 | 1 | balance | 65 | 85 | 92 |
| I | 15 | 2.75 | 2.5 | 1 | balance | 60 | 87 | 96 |
| J | 10 | 2.5 | 2.5 | 1 | balance | 75 | 87 | 95 |
| K | 15 | 2.5 | 2 | 1.1 | balance | 75 | 87 | 95 |
| L | 15 | 3 | 2.25 | 1 | balance | 50 | 84 | 93 |
| M | 20 | 2.5 | 2 | 0.8 | balance | 70 | 84 | 87 |
| N | 15 | 2.5 | 2 | 1 | balance | 75 | 82 | 87 |
| O | 20 | 2.5 | 2 | 1 | balance | 80 | 81 | 86 |
| P | 10 | 2.5 | 2 | 1 | balance | 70 | 81 | 85 |
| L | 20 | 2.5 | 1 | 1 | balance | 70 | 83 | 84 |
| M | 15 | 2.5 | 1.5 | 0.9 | balance | 70 | 83 | 83 |
| N | 20 | 2 | 1.5 | 1 | balance | 70 | 83 | 82 |

*based on a total weight of reactants
**mole ratio acid:quaternizable compound
***mole ratio quaternizing agent:quaternizable compound Thus, in some embodiments, the disclosed imide quats may be made by reacting a quaternizable compound, aprotic solvent, and an acid using the parameters shown in Table 3 below.

TABLE 3

| Protic solvent (may include water) | 0 to 30 wt %* |
|---|---|
| Water | 0 to 2.5 wt %* |
| Acid | 0:1 to 1.5:1** |
| Quaternizing agent | 0.5:1 to 3:1*** |
| Quaternizable compound | Balance |
| Temperature (quaternizing step) | 40 to 100° C. |

*based on a total weight of reactants
**mole ratio acid:quaternizable compound
***mole ratio quaternizing agent:quaternizable compound The ranges of the components used may vary based on reaction conditions, including batch size and time. For example, if propylene oxide is used as the quaternizing agent, large batches may require less propylene oxide than small batches because larger amounts of propylene oxide will not evaporate as quickly as smaller amounts. Further, some of the components, such as the protic solvent, water and/or acid are optional. Thus, it is possible to make the imide quats using parameters outside those disclosed in Tables 2 and 3.

The total amount of quat produced (Table 2) was measured using electrospray ionization mass spectrometry (ES-IMS) and nuclear magnetic resonance (NMR). The total amount of quat produced is the percentage of the quaternizable compound converted to the quaternized ammonium salt and may include both imide and amide quats. Thus, the amount of quaternizable compound converted or amount of quaternized salt produced, may range from 60 to 100%, or from 80 to 90%. The quaternized ammonium salt produced may comprise either all imide containing quaternized ammonium salts or a combination of imide and amide quats. For example, in one embodiment, 90% of the quaternized salt may be converted to a quat. All of the quat produced (100%) may be an imide quat. In another embodiment, the amount of quaternizable compound converted to imide quats may range from 25 to 100%. In another embodiment, the amount of quaternizable compound converted to imide quats may range from 30 to 70%, or 35 to 60%, with the balance including amide quats and/or unconverted quaternizable compound. Likewise, the amount of quaternizable compound converted may comprise 25 to 75% amide quats, with the balance comprising imide quats and and/or unconverted quaternizable compound.

Example 9—Formation of a 210 $M_n$ PIBSA/DMAPA Quaternary Ammonium Salt Using Propylene Oxide (an Imide/Propylene Oxide Quat)

For Example 9, an imide/propylene oxide quat is prepared as in Examples 1, 2, and 4, except that 210 $M_n$ polyisobutylene is used as the base material.

Comparative Example 10—Formation of a 1000 $M_n$ PIBSA/DMAPA Quaternary Ammonium Salt Using Propylene Oxide (1000$M_n$ Imide/Propylene Oxide Quat)

For Comparative Example 10, a 1000 $M_n$ imide/propylene oxide quat is prepared as in Example 5, except that 1000 $M_n$ polyisobutylene having greater than 70% vinylidene groups is used as the base material.

Example 11—Conventional 550 $M_n$ PIBSA

Conventional 550 PIB (2840 g, 5.163 moles) was charged to a 5 liter flange flask equipped with overhead stirrer, air condenser, nitrogen inlet, thermocouple and Eurotherm™ temperature controller (reaction kit).

Maleic anhydride (1138.8 g, 11.617 moles) was then charged to the reaction vessel. The batch was agitated under nitrogen blanket and slowly heated to 203° C. over a 90 minute period. The batch was maintained at 203° C. for 24 hours.

The reaction kit was then reconfigured for vacuum stripping. The batch was stripped at 210° C. and 0.05 bar to remove unreacted maleic anhydride. The batch comprising the formed PIBSA is filtered through a heated sinter funnel containing a pad of diatomaceous earth over 12 hours and then cooled back to 50° C. and decanted into a storage vessel.

Example 12—Formation of Quaternizable Compound—Conventional 550 $M_n$ PIBSA and Dimethylaminopropylamine (DMAPA)

The conventional 550 $M_n$ PIBSA (1520.2 g, 2.58 moles) (product of Example 11) is charged to a 3-liter flask equipped with a water condenser and Dean Stark trap, a thermocouple, a dropping funnel, an overhead stirrer and Nitrogen inlet and heated to 90° C.

DMAPA (268.0 g, 2.58 moles) is added to the flask via the dropping funnel over 50 minutes. The batch temperature is kept below 120° C. while adding the DMAPA.

Once all the DMAPA is added, the reaction is slowly heated to 150° C. and maintained at that temperature for 3 hours. Approximately 40 g of water is collected in the Dean Stark apparatus while heating. The remaining product is the 550 $M_n$ PIBSA/DMAPA quaternizable compound.

Example 13—Formation of a Conventional 550 $M_n$ PIBSA/DMAPA Quaternary Ammonium Salt Using Propylene Oxide (an Imide/Propylene Oxide Quat)

The 550 $M_n$ PIBSA/DMAPA quaternizable compound (545.3 g, 0.807 moles) (product of Example 14) is added to a 1-liter flask equipped with a water condenser, a thermocouple, a septum-needle syringe pump set-up, an overhead stirrer and nitrogen inlet.

2-ethylhexanol (124.7 g, 0.96 moles), acetic acid (48.4 g, 0.807 moles) and water (11.0 g, 0.61 moles) is also charged to the 1-liter flask.

The batch is then heated to 75° C., under agitation and nitrogen atmosphere. Propylene oxide (117.1 g, 2.02 moles) is added via a syringe pump over 4 hours. The batch is then held for 4 hours at 75° C. before being cooled back to 50° C. The imide/propylene oxide quat is then decanted into a storage vessel.

Deposit Tests—CEC F-23-01 Procedure for Diesel Engine Injector Nozzle Coking Test Deposit tests are performed using Peugeot S.A.'s XUD 9 engine in accordance with the procedure in CEC F-23-01. For the first deposit test, air flow is measured though clean injector nozzles of the XUD 9 engine using an air-flow rig. The engine is then run on a reference fuel (RF79) and cycled through various loads and speeds for a period of 10 hours to simulate driving and allow any formed deposits to accumulate. The air-flow through the nozzles are measured again using the air-flow rig. The percentage of air flow loss (or flow remaining) is then calculated.

A second deposit test is performed using the same steps above, except 7.5 ppm actives of the imide quat having a short hydrocarbon tail is added to the reference fuel. A third deposit test is performed using the same steps above, except 7.5 ppm actives of Comparative Example 10 is added to the reference fuel.

CEC F-98-08 DW10B Procedure for Common Rail Diesel Engine Nozzle Coking Test

Common rail fouling tests are performed using Peugeot S.A.'s DW10 2.0-liter common rail unit with a maximum injection pressure of 1600 bar and fitted with Euro standard 5 fuel injection equipment supplied by Siemens. The test directly measures engine power, which decreases as the level of injector fouling increases. The engine is cycled at high load and high speed in timed increments with "soak"

periods between the running cycles. The test directly measures engine power, which decreases as the level of injector fouling increases. For the first test, the engine is run on a reference fuel (RF79) with a trace amount of a zinc salt.

A second deposit test is performed using the same steps above, except 35 ppm of the imide quat having a short hydrocarbon tail is added to the reference fuel in addition to the zinc salt. A third deposit test is performed using the same steps as above, except 35 ppm of Comparative Example 10 is added to the reference fuel in addition to the zinc salt.

Additive Package Stability

To evaluate the effects of the molecular weight of imide quats on additive package stability, additive packages comprising a 550 $M_n$ PIBSA/DMAPA imide/propylene oxide quat (Example 12) and a mid-vinylidene (550 $M_n$) hydrolized polyisobutylene succinic anhydride ("HP") were prepared. Comparative additive packages comprising an 1000 $M_n$ imide quat (PIBSA/DMAPA imide/propylene oxide quat) (Comparative Example 10) and mid-vinylidene (550 $M_n$) hydrolized polyisobutylene succinic anhydride ("HP") were prepared. Additional additive packages were prepared as above, with 17.6 wt % of the stabilizing solvent (heavy aromatic naphtha or a mixture of heavy aromatic naphtha and 2-ethylhexanol) removed.

The additive packages tested are shown in Table 4 below. The amounts shown are in weight percents, based on a total weight of the additive package.

TABLE 4

| | Pack A wt % | Pack B wt % | Pack C wt % | Pack D wt % | Pack E wt % |
|---|---|---|---|---|---|
| Comparative Formulations | A-1 | B-1 | C-1 | D-1 | E-1 |
| 100 Mn Imide Quat | 10.712 | 19.852 | 19.822 | 18.116 | 36.970 |
| HP | 16.540 | 6.381 | 6.371 | 9.058 | 11.887 |
| Demulsifier 1[1] | | | | | ✓ |
| Demulsifier 2[2] | ✓ | ✓ | ✓ | ✓ | |
| Polydimethyl siloxane foam inhibitor[3] | ✓ | ✓ | ✓ | ✓ | |
| Heavy Aromatic Naphtha | 59.787 | 67.811 | 66.863 | 62.363 | 34.529 |
| 2-ethylhexanol | 10.551 | | | 6.929 | 14.973 |
| Total | 100.00 | 100.00 | 100.00 | 100.00 | 100.00 |
| Inventive Formulations | A-2 | B-2 | C-2 | D-2 | E-2 |
| 500 Mn Imide Quat | 10.712 | 19.852 | 19.822 | 18.116 | 36.970 |
| HP | 16.540 | 6.381 | 6.371 | 9.058 | 11.887 |
| Demulsifier 1 | | | | | ✓ |
| Demulsifier 2 | ✓ | ✓ | ✓ | ✓ | |
| Polydimethyl siloxane foam inhibitor[3] | ✓ | ✓ | ✓ | ✓ | |
| Heavy Aromatic Naphtha | 59.787 | 67.811 | 66.863 | 62.363 | 34.529 |
| 2-ethylhexanol | 10.551 | | | 6.929 | 14.973 |
| Total | 100.000 | 100.000 | 100.000 | 100.000 | 100.000 |
| Inventive Formulations (−17.6% solvent) | A-3 | B-3 | C-3 | D-3 | E-3 |
| 550 Mn Imide Quat | 12.230 | 22.551 | 22.474 | 20.640 | 40.509 |
| HP | 18.884 | 7.248 | 7.224 | 10.320 | 13.025 |
| Demulsifier 1[1] | | | | | ✓ |
| Demulsifier 2[2] | ✓ | ✓ | ✓ | ✓ | |
| Polydimethyl siloxane foam inhibitor[3] | ✓ | ✓ | ✓ | ✓ | |
| Heavy Aromatic Naphtha | 56.214 | 63.435 | 62.430 | 58.512 | 31.158 |
| 2-ethylhexanol | 9.920 | | | 6.502 | 13.511 |
| Total | 100.000 | 100.000 | 100.000 | 100.000 | 100.000 |

[1] Check mark indicates Demulsifier 1 was present in pack. The treat rate of Demulsifier 1 was the same for E-1, E-2, and E-3.
[2] Check mark indicates Demulsifier 2 was present in pack. While the treat rate of Demulsifier 2 differed between packs A, B, and C, the treat rate was constant between A-1, A-2, A-3, between B-1, B-2, B-3, and between C-1, C-2, C-3.
[3] Check mark indicates Polydimethyl siloxane foam inhibitor was present in pack. While the treat rate of foam inhibitor differed between packs A, B, and C, the treat rate was constant between A-1, A-2, A-3, between B-1, B-2, B-3, and between C-1, C-2, C-3.

Each additive package is placed in a separate graduated cylinder with a conical-shaped bottom and volume indicators. The cylinder is stored at −18° C. and the liquid drop out is measured at various intervals. These results are summarized in Table 5 below and in FIG. 1.

| | Additive Package A Drop out (mL) | Additive Package B Drop out (mL) | Additive Package C Drop out (mL) | Additive Package D Drop out (mL) | Additive Package E Drop out (mL) |
|---|---|---|---|---|---|
| 1000 Mn Quat + HP | 0.50 | 0.50 | 4.50 | 0.35 | 0.80 |
| 550 Mn Quat + HP | 0.15 | 0 | 0 | 0.07 | 0.12 |
| 550 Mn Quat + HP − 17.6% Solvent | 0.60 | 0.12 | 0.15 | 0.07 | 0 |

The results show that all of the package with 1000 Ma imide quat have greater than 0.2 ml liquid drop out. The equivalent packages with 550 $M_n$ imide quat all had less than 0.2 ml liquid drop out. Similarly, in the packages with the 17.6 wt % solvent removed, four of the five packages with the 550 $M_n$ imide quat were still more stable than the 1000 $M_n$ imide quat packages, showing that less solvent is required when using 550 $M_n$ imide quats.

Stability Tests Using HDSA/DMAPA Quaternary Ammonium Salt Using Propylene Oxide (an Imide/Propylene Oxide Quat) (Example 4)

Figure 2:
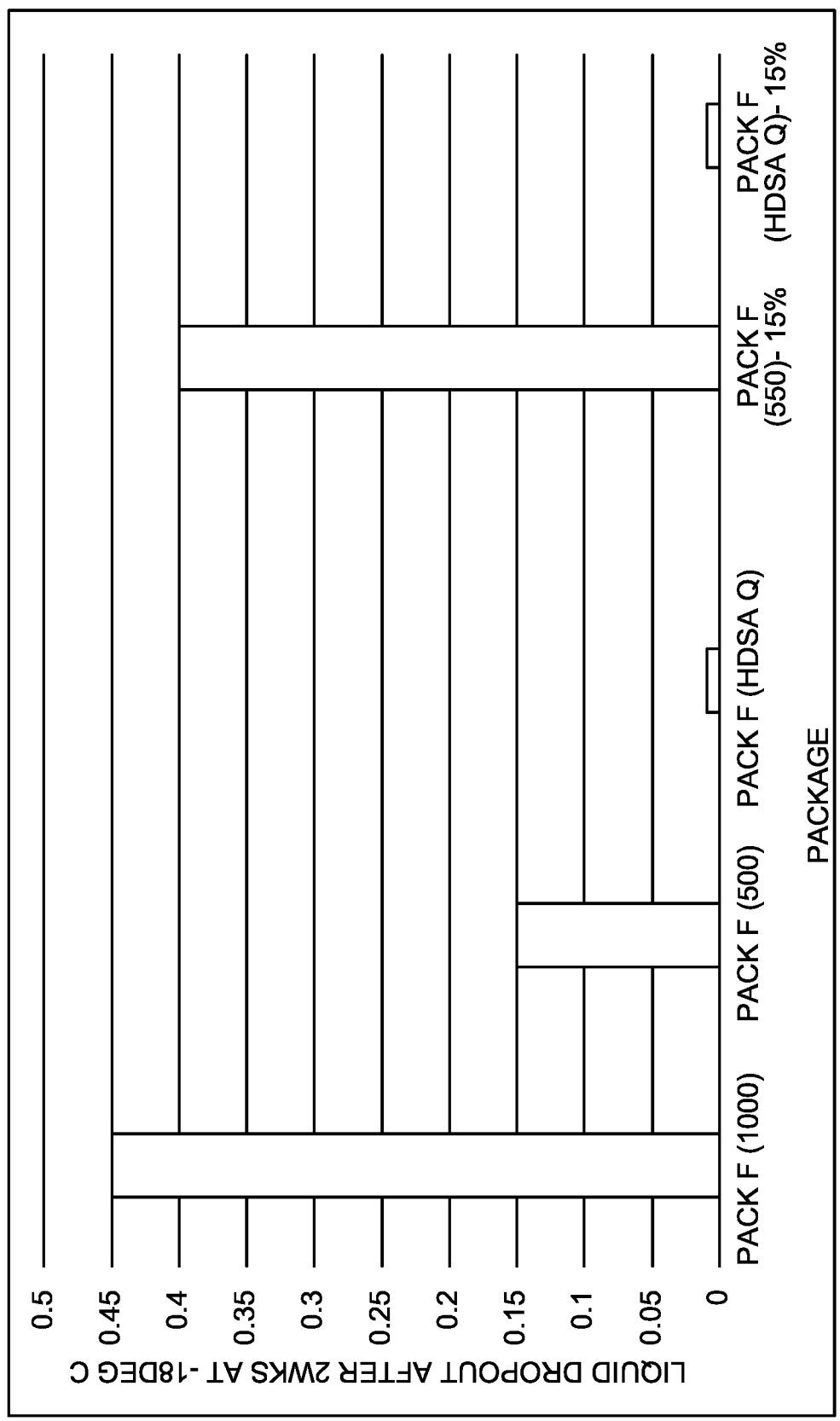
FIG. 2 shows the additive package stability test results of an embodiment of the disclosed technology.

Further testing showed that the additive packages may be even further improved when using the ultra-low molecular weight imide quats described herein. Additional samples (Additive Package F) were made and tested as described above, but the HDSA/DMAPA imide quat replaced the 550 $M_n$ PIBSA/DMAPA imide quat. The results for Additive Pack F are shown in FIG. 2.

| | Additive Pack F |
|---|---|
| HDSA/DMAPA Imide Quat | 10 to 20 |
| Hydrolyzed PIBSA | 10 to 20 |
| Commercial demulsifier | 1 to 2 |

-continued

|  | Additive Pack F |
| --- | --- |
| Polydimethyl siloxane foam inhibitor | 0.5 to 1.5 |
| Heavy Aromatic Naphtha | 50 to 65 |
| 2-Ethylhexanol | 5 to 15 |

Figure 3:
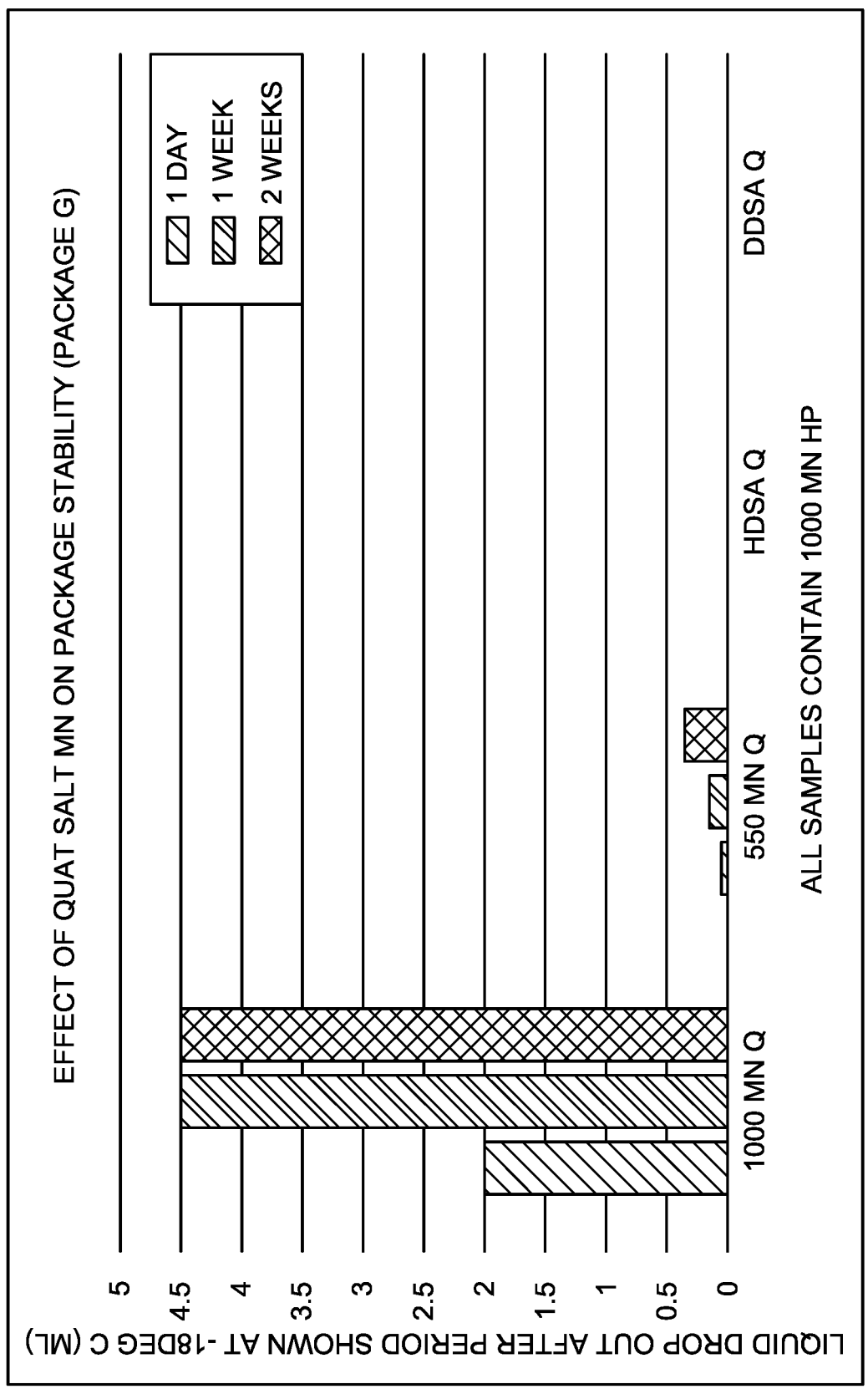
FIG. 3 shows the additive package stability test results of an embodiment of the disclosed technology.

Additional samples (Additive Package G) were made and tested as described above to compare 1000 $M_n$ quats, 550 $M_n$ quats, HDSA quats, and DDSA quats. The results for Additive Pack G are shown in FIG. 3

|  | Pack G Variants |
| --- | --- |
| Imide Quat | 20 to 30 |
| Hydrolyzed PIBSA | 5 to 10 |
| Commercial demulsifier | 5 to 10 |
| Polydimethyl siloxane foam inhibitor | 1 to 3 |
| Heavy Aromatic Naphtha | 60 to 70 |
| 2-Ethylhexanol | 0 |

Figure 4:
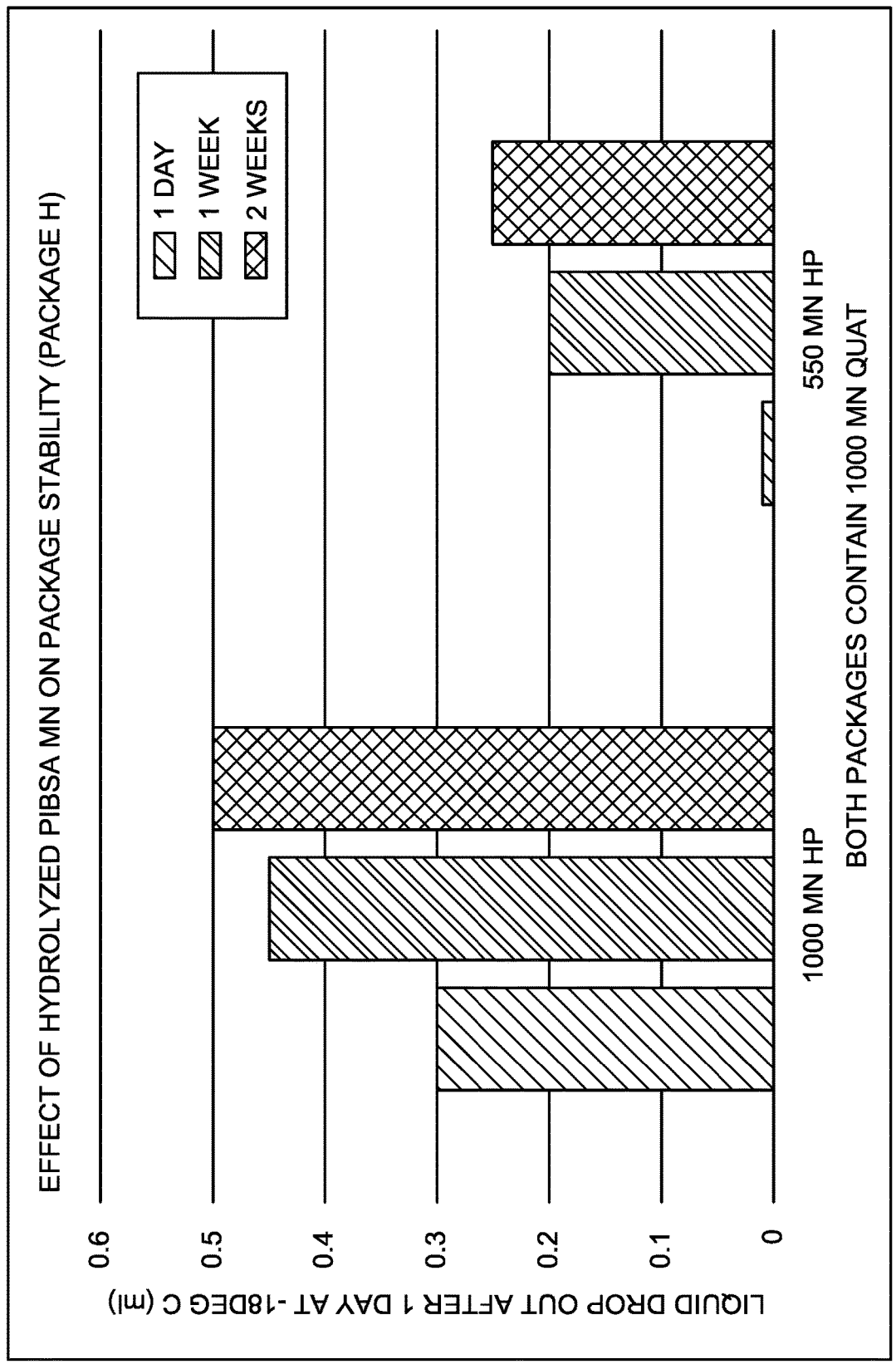
FIG. 4 shows the additive package stability test results of an embodiment of the disclosed technology.

Additional samples (Additive Package H) were made and tested as described above to compare the effects of different molecular weight PIBSA and package stability. The results for Additive Pack H are shown in FIG. 4.

|  | Pack H Variants |
| --- | --- |
| Imide Quat | 10 to 20 |
| Hydrolyzed PIBSA | 10 to 20 |
| Commercial demulsifier | 1 to 3 |
| Polydimethyl siloxane foam inhibitor | 0.5 to 2 |
| Heavy Aromatic Naphtha | 50 to 70 |
| 2-Ethylhexanol | 10 to 20 |

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention can be used together with ranges or amounts for any of the other elements.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the essential or basic and novel characteristics of the composition or method under consideration.

While certain representative embodiments and details have been shown for the purpose of illustrating the subject invention, it will be apparent to those skilled in this art that various changes and modifications can be made therein without departing from the scope of the subject invention. In this regard, the scope of the invention is to be limited only by the following claims.

What we claim:

1. A composition comprising an imide containing quaternary ammonium salt ("imide quat"), wherein the imide quat comprises the reaction product of:
   a) a quaternizable compound that is the reaction product of:
      (i) a hydrocarbyl-substituted acylating agent, wherein the hydrocarbyl-substituent has a number average molecular weight less than 300 and comprises at least one dodecenyl succinic anhydride, dodecenyl succinic acid, hexadecenyl succinic anhydride, hexadecenyl succinic acid, octadecenyl succinic anhydride, octadecenyl succinic acid, or mixtures thereof, and
      (ii) a nitrogen containing compound having a nitrogen atom capable of reacting with said hydrocarbyl-substituted acylating agent to form an imide, and further having at least one quaternizable amino group; and
   b) a quaternizing agent suitable for converting the quaternizable amino group of the nitrogen containing compound to a quaternary nitrogen.

2. The composition of claim 1, wherein the quaternizable amino group is a primary, secondary or tertiary amino group.

3. The composition of claim 1, wherein the quaternizing agent comprises at least one dialkyl sulfate, alkyl halide, hydrocarbyl substituted carbonate, hydrocarbyl epoxide, carboxylate, alkyl ester or mixtures thereof.

4. The composition of claim 1, further comprising a hydrolyzed alkenyl succinic acid or anhydride with a molecular weight $M_n$ ranging from about 225 to about 1000.

5. The composition of claim 4, wherein the hydrolyzed alkenyl succinic acid or anhydride has a $M_n$ of 1000.

6. The composition of claim 5, wherein the hydrolyzed alkenyl succinic acid or anhydride has a $M_n$ of 550.

7. A composition comprising an imide containing quaternary ammonium salt ("imide quat") and a hydrolyzed alkenyl succinic acid or anhydride with a molecular weight $M_n$ ranging from about 225 to about 1000, wherein the imide quat comprises the reaction product of:
   a) a quaternizable compound that is the reaction product of:
      (i) a hydrocarbyl-substituted acylating agent, wherein the hydrocarbyl-substituent has a number average molecular weight of less than 300 and comprises at least one dodecenyl succinic anhydride, dodecenyl succinic acid, hexadecenyl succinic anhydride, hexadecenyl succinic acid, octadecenyl succinic anhydride, octadecenyl succinic acid, or mixtures thereof, and (ii) a nitrogen containing compound having a nitrogen atom capable of reacting with said hydrocarbyl-substituted acylating agent to form an imide, and further having at least one quaternizable amino group; and b) a quaternizing agent suitable for converting the quaternizable amino group of the nitrogen containing compound to a quaternary nitrogen.

8. The composition of claim 1, further comprising a fuel that is liquid at room temperature.

9. The composition of claim 8 further comprising at least one of a low number average molecular weight soap, a low number average molecular weight polyisobutylene succinimide (PIBSI), or a mixture thereof.

10. The composition of claim 9, wherein said low number average molecular weight soap has a number average molecular weight ($M_n$) of less than 340.

11. The composition of claim 8, further comprising from 0.01 to 25 ppm of a metal and from 1 to 12 ppm of a corrosion inhibitor.

12. The composition of claim 11, wherein the corrosion inhibitor is an alkenyl succinic acid comprising at least one of dodecenyl succinic acid (DDSA), hexadecenyl succinic acid (HDSA), or mixtures thereof.

13. The composition of claim 9, wherein the low number average molecular weight PIBSI has an $M_n$ of less than 400.

14. A method of reducing and/or preventing injector deposits comprising:

c) supplying to a fuel injector of said engine:
  (i) a fuel, wherein said fuel
    1. is liquid at room temperature; and
    2. has a composition comprising an imide quat according to claim 1 therein; and d) operating said engine.

15. The method of claim 14, wherein the fuel comprises a low number average molecular weight soap, a low number average molecular weight polyisobutylene succinimide (PIBSI), or mixtures thereof.

16. The method of claim 15 wherein said low number average molecular weight soap has a number average molecular weight ($M_n$) of less than 340.

17. The method of claim 14 wherein the fuel comprises from 0.01 to 25 ppm of a metal and from 1 to 12 ppm of a corrosion inhibitor.

18. The method of claim 17 wherein the corrosion inhibitor is an alkenyl succinic acid comprising at least one of dodecenyl succinic acid (DDSA), hexadecenyl succinic acid (HDSA), or mixtures thereof.

19. The method of claim 15, wherein said low number average molecular weight PIBSI has an $M_n$ of less than 400.

* * * * *